US011383029B2

(12) United States Patent
Lang et al.

(10) Patent No.: US 11,383,029 B2
(45) Date of Patent: *Jul. 12, 2022

(54) SYSTEM FOR SYRINGE ENGAGEMENT TO AN INJECTOR

(71) Applicant: Bayer Healthcare LLC, Whippany, NJ (US)

(72) Inventors: Charles Lang, Pittsburgh, PA (US); Christopher Swenglish, Connellsville, PA (US); Luis Castillo, Oviedo, FL (US); Stephen Schulte, Gibsonia, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/404,272

(22) Filed: Aug. 17, 2021

(65) Prior Publication Data
US 2021/0369953 A1    Dec. 2, 2021

Related U.S. Application Data

(60) Continuation of application No. 17/073,574, filed on Oct. 19, 2020, now Pat. No. 11,103,637, which is a
(Continued)

(51) Int. Cl.
*A61M 5/145*   (2006.01)
*A61M 5/00*    (2006.01)

(52) U.S. Cl.
CPC .......... *A61M 5/1458* (2013.01); *A61M 5/007* (2013.01); *A61M 5/1456* (2013.01);
(Continued)

(58) Field of Classification Search
CPC ................ A61M 5/1458; A61M 5/007; A61M 5/14546; A61M 5/1456; A61M 5/14566; A61M 2205/3306; A61M 2205/581
See application file for complete search history.

(56) References Cited

U.S. PATENT DOCUMENTS 1,265,537 A    5/1918  Ivan
1,687,323 A   10/1928  Cook
(Continued)

FOREIGN PATENT DOCUMENTS

AU    317487       1/2008
CN   1876191 A    12/2006
(Continued)

OTHER PUBLICATIONS

Brochure for "Angiomat 6000" of Liebel-Farsheim, 2111 E. Galbraith Road, Cincinnati, OH 45215, © 1987.
(Continued)

*Primary Examiner* — Lauren P Farrar
*Assistant Examiner* — Hamza A Darb
(74) *Attorney, Agent, or Firm* — David Schramm; Joseph L. Kent; James R. Stevenson

(57) ABSTRACT

An injector system for injecting fluid includes a syringe and an injector. The syringe includes a body and a plunger movably disposed within the body. The plunger has at least one flexible leg extending toward the rearward end of the body. The injector has a housing with a front plate, a drive member at least partially disposed within the housing and operable to engage the plunger, and a syringe release assembly operable to release the syringe. The syringe assembly includes a syringe release gear that forms an enclosure for receiving the syringe when the syringe is fully seated within the housing and a plunger release tube surrounding at least a portion of the drive member. The plunger release tube has a first end rotationally engaged with the syringe release gear. Rotation of the syringe release assembly releases the at least one flexible leg from the drive member.

20 Claims, 13 Drawing Sheets

Related U.S. Application Data division of application No. 15/126,598, filed as application No. PCT/US2015/021171 on Mar. 18, 2015, now Pat. No. 10,806,852.

(60) Provisional application No. 61/970,018, filed on Mar. 25, 2014, provisional application No. 61/955,527, filed on Mar. 19, 2014.

(52) U.S. Cl.
CPC .... *A61M 5/14546* (2013.01); *A61M 5/14566* (2013.01); *A61M 2205/3306* (2013.01); *A61M 2205/581* (2013.01)

(56) References Cited

U.S. PATENT DOCUMENTS

| | | |
|---|---|---|
| 1,950,137 A | 3/1934 | Dowe |
| 1,988,480 A | 1/1935 | Campkin |
| 2,392,196 A | 1/1946 | Smith |
| 2,419,401 A | 4/1947 | Hinds |
| 2,702,547 A | 2/1955 | Glass |
| 2,842,126 A | 7/1958 | Brown |
| 3,051,173 A | 8/1962 | Johnson et al. |
| D203,730 S | 2/1966 | Porat |
| 3,270,483 A | 9/1966 | Smoyer et al. |
| 3,348,545 A | 10/1967 | Sarnoff et al. |
| 3,468,471 A | 9/1969 | Linder |
| 3,597,973 A | 8/1971 | Ryder |
| 3,604,417 A | 9/1971 | Stolzenberg et al. |
| 3,623,474 A | 11/1971 | Heilman et al. |
| 3,645,262 A | 2/1972 | Harrigan |
| 3,701,345 A | 10/1972 | Heilman et al. |
| 3,705,582 A | 12/1972 | Stumpf et al. |
| 3,719,306 A | 3/1973 | Holtzman |
| 3,720,211 A | 3/1973 | Kyrias |
| 3,738,539 A | 6/1973 | Beich |
| 3,752,145 A | 8/1973 | Runnells et al. |
| 3,796,218 A | 3/1974 | Burke et al. |
| 3,809,082 A | 5/1974 | Hurschman |
| 3,812,843 A | 5/1974 | Wooi et al. |
| 3,847,336 A | 11/1974 | Morris et al. |
| 3,902,491 A | 9/1975 | Lajus |
| 3,964,139 A | 6/1976 | Kleinmann et al. |
| 3,987,940 A | 10/1976 | Tischlinger |
| 3,998,224 A | 12/1976 | Chiquiar-Arias |
| 4,006,736 A | 2/1977 | Kranys et al. |
| 4,030,498 A | 6/1977 | Tompkins |
| 4,080,967 A | 3/1978 | O'Leary |
| 4,144,885 A | 3/1979 | Stait |
| 4,148,316 A | 4/1979 | Xanthopoulos |
| 4,155,490 A | 5/1979 | Glenn |
| 4,159,713 A | 7/1979 | Prais |
| 4,180,006 A | 12/1979 | Ross |
| 4,180,069 A | 12/1979 | Walters |
| 4,226,236 A | 10/1980 | Genese |
| 4,252,118 A | 2/1981 | Richard et al. |
| 4,278,086 A | 7/1981 | Hodgins et al. |
| 4,303,070 A | 12/1981 | Ichikawa et al. |
| 4,345,483 A | 8/1982 | Paletta et al. |
| 4,345,595 A | 8/1982 | Whitney et al. |
| 4,351,332 A | 9/1982 | Whitney et al. |
| 4,356,822 A | 11/1982 | Winstead-Hall |
| 4,384,581 A | 5/1983 | Conway |
| 4,424,720 A | 1/1984 | Bucchianeri |
| 4,452,251 A | 6/1984 | Heilman |
| 4,453,934 A | 6/1984 | Gahwiler et al. |
| 4,464,265 A | 8/1984 | Joyner |
| 4,465,472 A | 8/1984 | Urbaniak |
| 4,465,473 A | 8/1984 | Ruegg |
| 4,475,666 A | 10/1984 | Bilbrey et al. |
| 4,476,381 A | 10/1984 | Rubin |
| 4,490,256 A | 12/1984 | Nussbaumer et al. |
| 4,493,646 A | 1/1985 | Lacour et al. |
| 4,500,310 A | 2/1985 | Christinger |
| 4,529,401 A | 7/1985 | Leslie et al. |
| 4,562,844 A | 1/1986 | Carpenter et al. |
| 4,568,335 A | 2/1986 | Updike et al. |
| 4,573,978 A | 3/1986 | Reilly |
| 4,585,439 A | 4/1986 | Michel |
| 4,604,847 A | 8/1986 | Moulding, Jr. et al. |
| 4,612,010 A | 9/1986 | Hamacher et al. |
| 4,617,016 A | 10/1986 | Blomberg |
| 4,628,969 A | 12/1986 | Jurgens, Jr. et al. |
| 4,636,198 A | 1/1987 | Stade |
| 4,648,872 A | 3/1987 | Kamen |
| 4,650,475 A | 3/1987 | Smith et al. |
| 4,652,260 A | 3/1987 | Fenton, Jr. et al. |
| 4,664,128 A | 5/1987 | Lee |
| 4,676,776 A | 6/1987 | Howson |
| 4,677,980 A | 7/1987 | Reilly et al. |
| 4,677,981 A | 7/1987 | Coursant |
| 4,681,566 A | 7/1987 | Fenton, Jr. et al. |
| 4,685,903 A | 8/1987 | Cable et al. |
| 4,695,271 A | 9/1987 | Goethel |
| 4,705,509 A | 11/1987 | Stade |
| 4,718,463 A | 1/1988 | Jurgens, Jr. et al. |
| 4,722,734 A | 2/1988 | Kolln |
| 4,738,817 A | 4/1988 | Wittwer et al. |
| 4,741,732 A | 5/1988 | Crankshaw et al. |
| 4,741,736 A | 5/1988 | Brown |
| 4,749,109 A | 6/1988 | Kamen |
| 4,755,172 A | 7/1988 | Baldwin |
| 4,767,406 A | 8/1988 | Wadham et al. |
| 4,773,900 A | 9/1988 | Cochran |
| 4,791,290 A | 12/1988 | Noone et al. |
| 4,838,857 A | 6/1989 | Strowe et al. |
| 4,840,616 A | 6/1989 | Banks |
| 4,842,581 A | 6/1989 | Davis |
| RE32,974 E | 7/1989 | Porat et al. |
| 4,852,768 A | 8/1989 | Bartsch |
| 4,853,521 A | 8/1989 | Claeys et al. |
| 4,854,324 A | 8/1989 | Hirschman et al. |
| 4,863,427 A | 9/1989 | Cocchi |
| 4,869,720 A | 9/1989 | Chernack |
| 4,878,896 A | 11/1989 | Garrison et al. |
| 4,908,022 A | 3/1990 | Haber |
| 4,911,695 A | 3/1990 | Lindner |
| 4,923,443 A | 5/1990 | Greenwood et al. |
| 4,929,238 A | 5/1990 | Baum |
| 4,931,043 A | 6/1990 | Ray et al. |
| 4,932,941 A | 6/1990 | Min et al. |
| 4,936,833 A | 6/1990 | Sams |
| 4,943,279 A | 7/1990 | Samiotes et al. |
| 4,945,363 A | 7/1990 | Hoffman |
| 4,946,009 A | 8/1990 | Knutson |
| 4,950,243 A | 8/1990 | Estruch |
| 4,966,601 A | 10/1990 | Draenert |
| 4,969,874 A | 11/1990 | Michel et al. |
| 4,973,309 A | 11/1990 | Sultan |
| 4,978,335 A | 12/1990 | Arthur |
| 4,988,337 A | 1/1991 | Ito |
| 4,997,423 A | 3/1991 | Okuda et al. |
| 5,000,735 A | 3/1991 | Whelan |
| 5,007,904 A | 4/1991 | Densmore et al. |
| 5,019,045 A | 5/1991 | Lee |
| 5,024,663 A | 6/1991 | Yum |
| 5,033,650 A | 7/1991 | Colin et al. |
| 5,034,004 A | 7/1991 | Crankshaw |
| 5,047,014 A | 9/1991 | Mosebach et al. |
| 5,059,179 A | 10/1991 | Quatrochi et al. |
| 5,062,832 A | 11/1991 | Seghi |
| 5,066,859 A | 11/1991 | Karkar et al. |
| 5,078,683 A | 1/1992 | Sancoff et al. |
| 5,084,017 A | 1/1992 | Maffetone |
| 5,085,638 A | 2/1992 | Farbstein et al. |
| 5,085,643 A | 2/1992 | Larkin et al. |
| 5,090,962 A | 2/1992 | Landry, Jr. et al. |
| 5,093,079 A | 3/1992 | Bakaitis et al. |
| 5,094,148 A | 3/1992 | Haber et al. |
| 5,104,374 A | 4/1992 | Bishko et al. |
| 5,106,372 A | 4/1992 | Ran |
| 5,106,379 A | 4/1992 | Leap |
| D327,008 S | 6/1992 | Friedman |

(56) References Cited

U.S. PATENT DOCUMENTS

| | | |
|---|---|---|
| 5,122,118 A | 6/1992 | Haber et al. |
| 5,135,507 A | 8/1992 | Haber et al. |
| 5,147,311 A | 9/1992 | Pickhard |
| 5,153,827 A | 10/1992 | Coutre et al. |
| 5,176,642 A | 1/1993 | Clement |
| 5,181,912 A | 1/1993 | Hammett |
| 5,226,897 A | 7/1993 | Nevens et al. |
| 5,236,416 A | 8/1993 | McDaniel et al. |
| 5,242,408 A | 9/1993 | Jhuboo et al. |
| 5,246,423 A | 9/1993 | Farkas |
| 5,254,086 A | 10/1993 | Palmer et al. |
| 5,254,101 A | 10/1993 | Trombley, III |
| 5,256,154 A | 10/1993 | Liebert et al. |
| 5,256,157 A | 10/1993 | Samiotes et al. |
| 5,269,762 A | 12/1993 | Armbruster et al. |
| 5,275,582 A | 1/1994 | Wimmer |
| 5,279,569 A | 1/1994 | Neer et al. |
| 5,282,792 A | 2/1994 | Imbert |
| 5,282,858 A | 2/1994 | Bisch et al. |
| 5,300,031 A | 4/1994 | Neer et al. |
| 5,308,330 A | 5/1994 | Grimard |
| 5,314,415 A | 5/1994 | Liebert et al. |
| 5,317,506 A | 5/1994 | Coutre et al. |
| 5,324,273 A | 6/1994 | Discko, Jr. |
| 5,336,189 A | 8/1994 | Sealfon |
| 5,338,309 A | 8/1994 | Imbert |
| 5,342,298 A | 8/1994 | Michaels et al. |
| 5,353,691 A | 10/1994 | Haber et al. |
| 5,354,287 A | 10/1994 | Wacks |
| 5,356,375 A | 10/1994 | Higley |
| 5,356,393 A | 10/1994 | Haber et al. |
| 5,373,684 A | 12/1994 | Vacca |
| 5,380,285 A | 1/1995 | Jenson |
| 5,383,858 A | 1/1995 | Reilly et al. |
| 5,389,075 A | 2/1995 | Vladimirsky |
| 5,397,313 A | 3/1995 | Gross |
| 5,411,488 A | 5/1995 | Pagay et al. |
| 5,413,563 A | 5/1995 | Basile et al. |
| 5,425,716 A | 6/1995 | Kawasaki et al. |
| 5,429,602 A | 7/1995 | Hauser |
| 5,429,611 A | 7/1995 | Rait |
| 5,431,627 A | 7/1995 | Pastrone et al. |
| 5,433,712 A | 7/1995 | Stiles et al. |
| 5,439,452 A | 8/1995 | McCarty |
| 5,445,622 A | 8/1995 | Brown |
| 5,451,211 A | 9/1995 | Neer et al. |
| 5,456,670 A | 10/1995 | Neer et al. |
| 5,461,239 A | 10/1995 | Atherton |
| D364,461 S | 11/1995 | Liebert et al. |
| 5,478,314 A | 12/1995 | Malenchek |
| 5,484,413 A | 1/1996 | Gevorgian |
| 5,512,054 A | 4/1996 | Morningstar |
| 5,520,653 A | 5/1996 | Reilly et al. |
| 5,531,698 A | 7/1996 | Olsen |
| 5,531,710 A | 7/1996 | Dang et al. |
| 5,533,981 A | 7/1996 | Mandro et al. |
| 5,535,746 A | 7/1996 | Hoover et al. |
| 5,540,660 A | 7/1996 | Jenson |
| 5,545,140 A | 8/1996 | Conero et al. |
| 5,573,515 A | 11/1996 | Wilson et al. |
| 5,593,386 A | 1/1997 | Helldin |
| 5,624,408 A | 4/1997 | Helldin |
| D379,640 S | 6/1997 | Gilbert |
| 5,658,261 A | 8/1997 | Neer et al. |
| 5,662,612 A | 9/1997 | Niehoff |
| 5,681,285 A | 10/1997 | Ford et al. |
| 5,681,286 A | 10/1997 | Niehoff |
| 5,683,367 A | 11/1997 | Jordan et al. |
| 5,688,252 A | 11/1997 | Matsuda et al. |
| 5,695,477 A | 12/1997 | Sfikas |
| 5,722,951 A | 3/1998 | Marano |
| 5,735,825 A | 4/1998 | Stevens et al. |
| 5,738,655 A | 4/1998 | Vallelunga et al. |
| 5,738,659 A | 4/1998 | Neer et al. |
| 5,741,227 A | 4/1998 | Sealfon |
| 5,741,232 A | 4/1998 | Reilly et al. |
| 5,779,675 A | 7/1998 | Reilly et al. |
| 5,782,803 A | 7/1998 | Jentzen |
| 5,785,682 A | 7/1998 | Grabenkort |
| 5,795,333 A | 8/1998 | Reilly et al. |
| 5,795,337 A | 8/1998 | Grimard |
| 5,806,519 A | 9/1998 | Evans, III et al. |
| 5,807,321 A | 9/1998 | Stoker et al. |
| 5,807,334 A | 9/1998 | Hodosh et al. |
| 5,808,203 A | 9/1998 | Nolan, Jr. et al. |
| 5,827,219 A | 10/1998 | Uber, III et al. |
| 5,827,262 A | 10/1998 | Neftel et al. |
| 5,840,026 A | 11/1998 | Uber, III et al. |
| RE35,979 E | 12/1998 | Reilly et al. |
| 5,843,037 A | 12/1998 | Uber, III |
| D403,762 S | 1/1999 | Gabbard et al. |
| 5,858,239 A | 1/1999 | Kenley et al. |
| 5,865,805 A | 2/1999 | Ziemba |
| 5,873,861 A | 2/1999 | Hitchins et al. |
| D407,362 S | 3/1999 | Schardt |
| 5,879,336 A | 3/1999 | Brinon |
| 5,882,343 A | 3/1999 | Wilson et al. |
| 5,899,885 A | 5/1999 | Reilly et al. |
| 5,902,276 A | 5/1999 | Namey, Jr. |
| 5,913,844 A | 6/1999 | Ziemba et al. |
| 5,916,197 A | 6/1999 | Reilly et al. |
| 5,919,167 A | 7/1999 | Mulhauser et al. |
| 5,928,197 A | 7/1999 | Niehoff |
| D412,635 S | 8/1999 | Eiling |
| 5,938,637 A | 8/1999 | Austin et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Kazousky et al. |
| 5,954,697 A | 9/1999 | Srisathapat et al. |
| 5,954,700 A | 9/1999 | Kovelman |
| 5,997,502 A | 12/1999 | Reilly et al. |
| 5,997,511 A | 12/1999 | Curie et al. |
| 6,004,292 A | 12/1999 | Battiato et al. |
| 6,004,300 A | 12/1999 | Butcher et al. |
| 6,017,330 A | 1/2000 | Hitchins et al. |
| 6,019,745 A | 2/2000 | Gray |
| 6,042,565 A | 3/2000 | Hirschman et al. |
| 6,048,334 A | 4/2000 | Hirschman et al. |
| D424,198 S | 5/2000 | Shepherd et al. |
| 6,059,756 A | 5/2000 | Yeh |
| 6,080,136 A | 6/2000 | Trull et al. |
| 6,083,197 A | 7/2000 | Umbaugh |
| 6,083,200 A | 7/2000 | Grimm et al. |
| 6,090,064 A | 7/2000 | Reilly et al. |
| 6,099,502 A | 8/2000 | Duchon et al. |
| 6,129,712 A | 10/2000 | Sudo et al. |
| 6,142,976 A | 11/2000 | Kubo |
| 6,162,200 A | 12/2000 | Sawa et al. |
| 6,196,999 B1 | 3/2001 | Goethel et al. |
| 6,221,045 B1 | 4/2001 | Duchon et al. |
| 6,221,051 B1 | 4/2001 | Hjertman et al. |
| 6,224,577 B1 | 5/2001 | Dedola et al. |
| 6,267,749 B1 | 7/2001 | Miklos et al. |
| D447,799 S | 9/2001 | Jun |
| 6,290,678 B1 | 9/2001 | Aydelotte et al. |
| 6,312,410 B1 | 11/2001 | Yamamoto |
| 6,315,758 B1 | 11/2001 | Neer et al. |
| 6,322,535 B1 | 11/2001 | Hitchins et al. |
| RE37,487 E | 12/2001 | Reilly et al. |
| 6,332,877 B1 | 12/2001 | Michels |
| 6,336,913 B1 | 1/2002 | Spohn et al. |
| 6,339,718 B1 | 1/2002 | Zatezalo et al. |
| 6,345,262 B1 | 2/2002 | Madden |
| 6,368,307 B1 | 4/2002 | Ziemba et al. |
| 6,432,089 B1 | 8/2002 | Kakimi et al. |
| 6,447,487 B1 | 9/2002 | Cane' |
| 6,511,459 B1 | 1/2003 | Fago |
| 6,517,516 B1 | 2/2003 | Caizza |
| 6,533,183 B2 | 3/2003 | Aasmul et al. |
| 6,533,758 B1 | 3/2003 | Staats et al. |
| 6,569,127 B1 * | 5/2003 | Fago ............... A61M 5/14546 604/131 |
| 6,582,399 B1 | 6/2003 | Smith et al. |

(56) References Cited

U.S. PATENT DOCUMENTS

| | | |
|---|---|---|
| 6,585,700 B1 | 7/2003 | Trocki et al. |
| 6,626,862 B1 | 9/2003 | Duchon et al. |
| 6,652,489 B2 | 11/2003 | Trocki et al. |
| 6,659,979 B2 | 12/2003 | Neer et al. |
| 6,669,663 B1 | 12/2003 | Thompson |
| 6,676,635 B2 | 1/2004 | Nemoto |
| 6,726,657 B1 | 4/2004 | Dedig et al. |
| 6,733,477 B2 | 5/2004 | Cowan et al. |
| 6,733,478 B2 | 5/2004 | Reilly et al. |
| 6,743,202 B2 | 6/2004 | Hirschman et al. |
| 6,752,789 B2 | 6/2004 | Duchon et al. |
| 6,764,466 B1 | 7/2004 | Staats et al. |
| 6,808,513 B2 | 10/2004 | Reilly et al. |
| 6,817,990 B2 | 11/2004 | Yap et al. |
| 6,958,053 B1 | 10/2005 | Reilly |
| 7,018,363 B2 | 3/2006 | Cowan et al. |
| 7,025,757 B2 | 4/2006 | Reilly et al. |
| 7,029,459 B2 | 4/2006 | Reilly |
| 7,094,216 B2 | 8/2006 | Trombley, III et al. |
| 7,240,882 B2 | 7/2007 | Degentesh et al. |
| 7,264,612 B2 | 9/2007 | Nemoto |
| D555,802 S | 11/2007 | Coulling et al. |
| 7,300,417 B1 | 11/2007 | Goethel et al. |
| 7,337,538 B2 | 3/2008 | Moutafis et al. |
| 7,344,520 B2 | 3/2008 | Nemoto |
| 7,393,341 B2 | 7/2008 | Nemoto |
| 7,399,293 B2 | 7/2008 | Oyibo et al. |
| 7,419,478 B1 | 9/2008 | Reilly et al. |
| 7,455,659 B2 | 11/2008 | Nemoto et al. |
| 7,462,166 B2 | 12/2008 | Kowan et al. |
| 7,497,843 B1 | 3/2009 | Castillo et al. |
| 7,501,092 B2 | 3/2009 | Chen |
| 7,503,906 B2 | 3/2009 | Nemoto |
| 7,540,856 B2 | 6/2009 | Hitchins |
| 7,549,977 B2 | 6/2009 | Schriver et al. |
| 7,553,294 B2 | 6/2009 | Lazzaro et al. |
| 7,556,619 B2 | 7/2009 | Spohn et al. |
| 7,566,326 B2 | 7/2009 | Duchon et al. |
| 7,666,169 B2 | 2/2010 | Cowan et al. |
| 7,682,345 B2 | 3/2010 | Savage |
| 7,691,085 B2 | 4/2010 | Dedig et al. |
| 7,695,457 B2 | 4/2010 | Nemoto |
| 7,753,885 B2 | 7/2010 | Duchon et al. |
| 7,775,990 B2 | 8/2010 | DeHart |
| 7,803,134 B2 | 9/2010 | Sharifi et al. |
| 7,854,726 B2 | 12/2010 | Fago et al. |
| 7,875,005 B2 | 1/2011 | Nemoto |
| D632,389 S | 2/2011 | Maeda et al. |
| D632,784 S | 2/2011 | Maeda et al. |
| D637,492 S | 5/2011 | Baird et al. |
| 7,937,134 B2 | 5/2011 | Uber et al. |
| 7,972,306 B2 | 7/2011 | Shearn |
| 7,998,133 B2 | 8/2011 | Fago et al. |
| 8,012,124 B1 | 9/2011 | Fago et al. |
| 8,012,125 B1 | 9/2011 | Fago et al. |
| 8,038,656 B2 | 10/2011 | Lloyd et al. |
| 8,070,732 B2 | 12/2011 | Rochette |
| 8,105,293 B2 | 1/2012 | Pickhard |
| 8,133,203 B2 | 3/2012 | Hack |
| 8,147,464 B2 | 4/2012 | Spohn et al. |
| 8,173,995 B2 | 5/2012 | Ramakrishnan et al. |
| 8,177,757 B2 | 5/2012 | Nemoto et al. |
| D665,498 S | 8/2012 | Tamura et al. |
| 8,262,644 B2 | 9/2012 | Fago et al. |
| D668,331 S | 10/2012 | Ren et al. |
| 8,308,689 B2 | 11/2012 | Lewis |
| 8,337,456 B2 | 12/2012 | Schriver et al. |
| 8,353,879 B2 | 1/2013 | Goethel et al. |
| 8,403,909 B2 | 3/2013 | Spohn et al. |
| 8,454,560 B2 | 6/2013 | Strobl |
| D686,322 S | 7/2013 | Maeda et al. |
| 8,475,415 B2 | 7/2013 | Schiller et al. |
| 8,480,631 B2 | 7/2013 | Wotton et al. |
| 8,506,523 B2 | 8/2013 | Miyazaki et al. |
| 8,574,200 B2 | 11/2013 | Hack |
| 8,585,658 B2 | 11/2013 | Forstreuter |
| 8,597,246 B1 | 12/2013 | Fago et al. |
| 8,613,730 B2 | 12/2013 | Hieb et al. |
| 8,628,495 B2 | 1/2014 | Horton et al. |
| 8,800,071 B2 | 8/2014 | Sanchez Moreno |
| D745,668 S | 12/2015 | Shiraishi et al. |
| D787,668 S | 5/2017 | Ishida et al. |
| D788,296 S | 5/2017 | Ishida et al. |
| D788,297 S | 5/2017 | Ishida et al. |
| D788,912 S | 6/2017 | Ishida et al. |
| D792,206 S | 7/2017 | Baiz et al. |
| D793,220 S | 8/2017 | Baiz et al. |
| D793,854 S | 8/2017 | Baiz et al. |
| D826,397 S | 8/2018 | Green |
| D848,756 S | 5/2019 | Ren |
| 11,103,637 B2 * | 8/2021 | Lang ................... A61M 5/1456 |
| 2002/0071920 A1 | 6/2002 | Obeshaw |
| 2002/0165491 A1 * | 11/2002 | Reilly ............... A61M 5/14546 |
| | | 604/154 |
| 2003/0004468 A1 | 1/2003 | Righi et al. |
| 2003/0009133 A1 | 1/2003 | Ramey |
| 2003/0065287 A1 | 4/2003 | Spohn et al. |
| 2003/0120219 A1 | 6/2003 | Nielsen et al. |
| 2003/0153877 A1 | 8/2003 | Huang et al. |
| 2003/0163089 A1 | 8/2003 | Bynum |
| 2003/0216683 A1 | 11/2003 | Shekalim |
| 2003/0236800 A1 | 12/2003 | Goeltzenleuchter et al. |
| 2004/0006314 A1 | 1/2004 | Campbell et al. |
| 2004/0039368 A1 | 2/2004 | Reilly et al. |
| 2004/0068223 A1 | 4/2004 | Reilly |
| 2004/0074453 A1 | 4/2004 | Roelle et al. |
| 2004/0116861 A1 | 6/2004 | Trocki et al. |
| 2004/0133153 A1 | 7/2004 | Trocki et al. |
| 2004/0133161 A1 | 7/2004 | Trocki et al. |
| 2004/0133183 A1 | 7/2004 | Trocki et al. |
| 2004/0186437 A1 | 9/2004 | Frenette et al. |
| 2004/0243022 A1 | 12/2004 | Carney et al. |
| 2004/0243067 A1 | 12/2004 | Sibbitt |
| 2005/0063857 A1 | 3/2005 | Alheidt et al. |
| 2005/0080384 A1 | 4/2005 | Green, Jr. |
| 2005/0240149 A1 | 10/2005 | Lu |
| 2006/0084925 A1 | 4/2006 | Ramsahoye |
| 2006/0129104 A1 | 6/2006 | Cowan et al. |
| 2006/0173411 A1 | 8/2006 | Barere |
| 2007/0123830 A1 | 5/2007 | Johannes Fierkens, Sr. et al. |
| 2007/0191785 A1 | 8/2007 | Barere et al. |
| 2007/0203460 A1 | 8/2007 | Nemoto et al. |
| 2008/0086087 A1 | 4/2008 | Spohn et al. |
| 2008/0167615 A1 | 7/2008 | Niehoff |
| 2008/0306443 A1 | 12/2008 | Neer et al. |
| 2009/0188311 A1 | 7/2009 | Cadieux et al. |
| 2009/0247957 A1 | 10/2009 | Heutschi |
| 2010/0013096 A1 | 1/2010 | Irumata et al. |
| 2010/0016796 A1 | 1/2010 | Derichs |
| 2010/0057014 A1 | 3/2010 | Cane et al. |
| 2010/0280370 A1 | 11/2010 | Namey, Jr. |
| 2010/0318030 A1 | 12/2010 | Jenkins |
| 2011/0034882 A1 | 2/2011 | Quinn et al. |
| 2011/0056290 A1 | 3/2011 | Bryant et al. |
| 2011/0178500 A1 | 7/2011 | Shang et al. |
| 2011/0208350 A1 | 8/2011 | Eliuk et al. |
| 2011/0224611 A1 | 9/2011 | Lum et al. |
| 2012/0039809 A1 | 2/2012 | Levinson et al. |
| 2012/0104256 A1 | 5/2012 | Rapoport et al. |
| 2012/0127290 A1 | 5/2012 | Tojo et al. |
| 2012/0172817 A1 | 7/2012 | Bruggemann et al. |
| 2012/0184920 A1 | 7/2012 | Okihara et al. |
| 2012/0286187 A1 | 11/2012 | Spolski |
| 2013/0150806 A1 | 6/2013 | Fangrow, Jr. |
| 2013/0150821 A1 | 6/2013 | Bollish et al. |
| 2013/0211325 A1 | 8/2013 | Wang et al. |
| 2013/0310756 A1 | 11/2013 | Whalley et al. |
| 2013/0317427 A1 | 11/2013 | Brereton et al. |
| 2013/0317480 A1 | 11/2013 | Reber et al. |
| 2013/0338605 A1 | 12/2013 | Chen |
| 2014/0027009 A1 | 1/2014 | Riley et al. |

(56) References Cited

U.S. PATENT DOCUMENTS

| | | | |
|---|---|---|---|
| 2014/0031763 A1 | 1/2014 | Soma et al. | |
| 2014/0045668 A1 | 2/2014 | Case et al. | |

FOREIGN PATENT DOCUMENTS

| | | | |
|---|---|---|---|
| CN | 101801442 A | 8/2010 | |
| DE | 2919978 A1 | 11/1980 | |
| DE | 3227417 A1 | 2/1983 | |
| DE | 4017920 A1 | 12/1991 | |
| DE | 4319115 A1 | 12/1994 | |
| DE | 19601214 A1 | 8/1996 | |
| DE | 19633530 A1 | 2/1998 | |
| EP | 0111724 A2 | 6/1984 | |
| EP | 0160303 A2 | 11/1985 | |
| EP | 0164904 A2 | 12/1985 | |
| EP | 0308380 A2 | 3/1989 | |
| EP | 0319275 A1 | 6/1989 | |
| EP | 0320168 A1 | 6/1989 | |
| EP | 0323321 A1 | 7/1989 | |
| EP | 0346950 A2 | 12/1989 | |
| EP | 0364010 A2 | 4/1990 | |
| EP | 0384657 A1 | 8/1990 | |
| EP | 0482677 A1 | 4/1992 | |
| EP | 0523343 A1 | 1/1993 | |
| EP | 0523434 A1 | 1/1993 | |
| EP | 0567944 A1 | 11/1993 | |
| EP | 0567945 A1 | 11/1993 | |
| EP | 0584531 A2 | 3/1994 | |
| EP | 0736306 A1 | 10/1996 | |
| EP | 0749757 A2 | 12/1996 | |
| EP | 0900573 A2 | 3/1999 | |
| EP | 0919251 A2 | 6/1999 | |
| EP | 0951306 A2 | 10/1999 | |
| EP | 1002551 A2 | 5/2000 | |
| EP | 1166807 A1 | 1/2002 | |
| EP | 1932555 A1 | 6/2008 | |
| EP | 2327431 A1 | 6/2011 | |
| GB | 847914 A | 9/1960 | |
| GB | 1380873 A | 1/1975 | |
| GB | 2108852 A | 5/1983 | |
| JP | S61500415 A | 3/1986 | |
| JP | S6327770 A | 2/1988 | |
| JP | S6368177 A | 3/1988 | |
| JP | 2001029466 A | 2/2001 | |
| JP | 1462798 B2 | 5/2010 | |
| JP | D1398129 | 10/2010 | |
| JP | D1398130 | 10/2010 | |
| JP | D1400385 | 11/2010 | |
| JP | D1400386 | 11/2010 | |
| JP | D1400551 | 11/2010 | |
| JP | D1400552 | 11/2010 | |
| TW | 358742 B | 5/1999 | |
| WO | 8002376 A1 | 11/1980 | |
| WO | 8500292 A1 | 1/1985 | |
| WO | 8502256 A1 | 5/1985 | |
| WO | 8906145 A1 | 7/1989 | |
| WO | 8909071 A1 | 10/1989 | |
| WO | 8911310 A1 | 11/1989 | |
| WO | 9001962 A1 | 3/1990 | |
| WO | 9104759 A1 | 4/1991 | |
| WO | 9221391 A1 | 12/1992 | |
| WO | 9413336 A1 | 6/1994 | |
| WO | 9425089 A1 | 11/1994 | |
| WO | 9632975 A1 | 10/1996 | |
| WO | 9707841 A2 | 3/1997 | |
| WO | 9736635 A1 | 10/1997 | |
| WO | 9800187 A1 | 1/1998 | |
| WO | 9820920 A2 | 5/1998 | |
| WO | 9965548 A1 | 12/1999 | |
| WO | 0108727 A1 | 2/2001 | |
| WO | 0137903 A2 | 5/2001 | |
| WO | 0137905 A2 | 5/2001 | |
| WO | 0204049 A1 | 1/2002 | |
| WO | 02056934 A2 | 7/2002 | |
| WO | 02081011 A1 | 10/2002 | |
| WO | 03101527 A1 | 12/2003 | |
| WO | 2004035289 A1 | 4/2004 | |
| WO | 2005053771 A2 | 6/2005 | |
| WO | 2007064234 A1 | 6/2007 | |
| WO | 2007130061 A1 | 11/2007 | |
| WO | 2008051576 A2 | 5/2008 | |
| WO | 2009025996 A1 | 2/2009 | |
| WO | 2009036496 A2 | 3/2009 | |
| WO | 2010139793 A1 | 12/2010 | |
| WO | 2011129175 A1 | 10/2011 | |
| WO | 2012124028 A1 | 9/2012 | |
| WO | 2012155035 A1 | 11/2012 | |

OTHER PUBLICATIONS

Brochure for "Angiomat CT" of Liebel-Farsheim, 2111 E. Galbraith Road, Cincinnati, OH 45215, © 1988.

Brochure for "Cordis Lymphography Injector," Cordis Corporation, Miami, FL 33137 (1972).

Brochure for "PercuPump 1A" of E-Z-Em, Inc, 717 Main Street, Westbury, NY 11590, © 1990.

Brochure for the "The First and Only True Injection System," Medrad Mark V System, Control No. 85106-00-BA-02, Nov. 1988.

Comar., "Oral Syringes", Jul. 2015.

Human; Engineering Branch., "Field Study of Detectability of Colored Targets at Sea", U.S. Naval Medical Research Laboratory, May 26, 1955, vol. XIV, No. 5.

Injektron 82 MRT User Instructions, Version MR2, CEO535, Med-Tron GmbH(Mar. 10, 1999).

"International Preliminary Report on Patentability from Corresponding PCT Application No. PCT/US2015/021171", dated Sep. 20, 2016.

"International Search Report and Written Opinion from corresponding PCT Application No. PCT/US2015/021171", dated Jun. 23, 2015.

Italian Patent Application No. 101995900431047 filed Mar. 28, 1995 and published Sep. 28, 1996 entitled "Syringe Actuator Gun".

Italian Patent Application No. 101995900437124 filed Apr. 27, 1995 and published Oct. 27, 1996 entitled "Syringe for the Injection of Large Quantities of Liquid, Such as Disinfectant, Preservative, Medicinal Liquids or the Like".

Italian Patent Application No. 101997900585879 filed Mar. 28, 1997 and published Sep. 28, 1998 entitled "Bayonet Connection Between a Spray Pump and a Bottle of a Substance Tobe Sprayed".

Italian Patent Application No. 101999900781373 filed Aug. 13, 1999 and published Feb. 13, 2001, entitled "Device for the Infusion of Drugs".

Italian Patent Application No. 101999900809451 filed Dec. 21, 1999 and published Jun. 21, 2001, entitled "Syringe for the Infusion of Drugs".

Italian Patent Application No. 201998900725470 filed Dec. 18, 1998 and published Jun. 18, 2000 entitled "Solenoid Valve With Sleeve Provided With Bayonet Mount and Means to Lockit in Position".

Liebel-Flarsheim company—Angiomat 6000 Digital Injection System Operator's Manual, 600950 Rev 1 (1990); p. 3-6 to 3-8, 4-52 to 4-56.

Mallinckrodt; Pharmaceuticals., "Power Injectors for Diagnostic Imaging", 2013.

Marc; Green PHD, "Visual Expert Human Factors: Color Functionality in Tradedress: A Case Example", 2013.

Medrad Envision CT Injector Operation Manual, EOM 700E, 92401-T-123 Rev E, Copyright 1995.

Medrad Envision CT Injector Operation Manual, EOM 700E, 92401-T-123 Rev E, pp. 2-10 to 2-11 and pp. 2-30 to 2-35(Copyright 1995).

Medrad, Mark V/Mark V Plus Injector Operation Manual,KMP 805P Rev. B (1990); pp. 1-18 to 1-28, 3-7 to 3-13, 14-1 to 14-4.

Medtron; Ag., "Injektron CT 2, Computer Tomography", 2004.

Sidam; Medical Devices., "Injector Syringe With Automatic Three-Way Valve".

"Supplementary European Search Report in EP App. EP15765821", dated Oct. 24, 2017.

(56) References Cited

OTHER PUBLICATIONS

"Why Lime-Yellow Fire Trucks Are Safer Than Red", American Psychological Association, Feb. 2014.

* cited by examiner

SYSTEM FOR SYRINGE ENGAGEMENT TO AN INJECTOR

CROSS REFERENCE TO RELATED APPLICATION

This application is a Continuation Application of U.S. application Ser. No. 17/073,574, filed Oct. 19, 2020, now U.S. Pat. No. 11,103,637, issued on Aug. 31, 2021, which is a Divisional Application of U.S. application Ser. No. 15/126, 598, filed Sep. 16, 2016, now U.S. Pat. No. 10,806,852, which is a 371 Application of International Application No. PCT/US2015/21171, filed Mar. 18, 2015, which claims priority to U.S. Provisional Application No. 61/955,527, filed Mar. 19, 2014 and U.S. Provisional Application No. 61/970,018, filed on Mar. 25, 2014, the disclosures of which are incorporated herein by reference in their entirety.

BACKGROUND

Field

This application relates to medical injectors and syringes, syringe interfaces, and syringe plungers for use therewith. More particularly, the present application relates to front-loading medical injectors and syringes, syringe interfaces, and syringe plungers for use with new or existing medical injectors such that the syringe is mountable upon and removable from the injectors by a syringe latch.

Description of Related Art

Medical injectors and syringes for injecting contrast media into a patient for imaging biological structures are known in the art. For example, with reference to FIG. 1, a conventional injector apparatus 10 for injecting a liquid contrast media into a vascular system of an animal is disclosed in U.S. Pat. No. 5,383,858, which is incorporated herein by reference. This injector apparatus 10 has a front-loading construction. The apparatus of FIG. 1 utilizes a syringe 12 capable of being front-loaded into a mounting assembly 14 associated with a front wall 16 of a housing 18 of an injector 20 by a first releasable mechanism 22. The syringe 12 is capable of functioning in an injection operation without the use of a pressure jacket (although the syringe may be used in an injector with a pressure jacket).

With continued reference to FIG. 1, the mounting assembly 14 is provided with an essentially cylindrical interface 26 for receiving a rearward end of the syringe 12. The interface 26 includes an annular surface 28, which may be cylindrical or conically tapered. The annular surface 28 includes a distal ledge, which is engaged by tabs 30 on the rearward end of the syringe 12. The syringe 12 is inserted into the cylindrical interface 26 until the tabs 30 engage the distal ledge to secure the syringe 12 to the injector 20.

The syringe 12 comprises an elongated main tubular body or barrel 32 and a coaxial discharge injection section 34, interconnected by an intermediate conical portion 36. A plunger 38 is slidably positioned within the tubular body 32 and is connectable to a second releasable mechanism 40 on a piston 42 in the injector housing 18. The second releasable mechanism 40 is formed in part by the plunger 38 and in part by the piston 42.

The piston 42 and plunger 38 cooperate to eject fluid contained within the syringe 12 in a desired quantity and at a desired rate. The second releasable mechanism 40 is designed to facilitate axial movement of the plunger 38 in either direction when actuated. The second releasable mechanism 40 is also designed to engage or disengage the plunger 38 from the piston 42 no matter where the plunger 38 sits in tubular body 32.

In operation, the syringe 12 is mounted by inserting the syringe 12 into the interface 26 in the mounting assembly 14. The tabs 30 initially move past the annular surface 28 where they engage the distal ledge to securely hold the syringe 12 to the mounting assembly 14. The mounting assembly 14 further includes a forwardly projecting annular ring or collar 44, which functions to assure perpendicular engagement between the plunger 38 and piston 42. As explained above, the forwardly projecting annular ring or collar 44 also functions as a seal between a resilient annular sealing flange 46 on the syringe 12 and the mounting assembly 14.

The resilient annular sealing flange 46 surrounds the tubular body 32 of the syringe 12 and is disposed forward of the tabs 30 a preselected distance essentially equal to a width of the annular surface 28. Thus, when the syringe 12 is inserted into the interface 26 in the mounting assembly 14 until the sealing flange 46 engages the annular ring 44, the annular ring 44 and flange 46 create a seal between the syringe 12 and the mounting assembly 14.

With further reference to FIG. 1, the apparatus also includes a system for transmitting syringe information from the syringe 12 to an injector controller 51. The syringe 12 is provided with an encoding device 48 forward of the tabs 30 but rearward of the flange 46. When attaching the syringe 12 to the mounting assembly 14, if the syringe 12 is rotated after the tabs 30 engage the distal ledge, a sensor 50 is provided in the annular surface 28 to read the encoding device 48. The sensor 50 then forwards the associated signals to the injector controller 51, which interprets the signals and modifies the function of the injector 20 accordingly. Examples of the information which could be encoded on the encoding device 48 include dimensions of the syringe 12, volume of the syringe 12, content of the syringe 12 (in the case of a pre-filled syringe), manufacturing information such as lot numbers, dates and tool cavity number, recommended contrast media flow rates and pressures, and loading/injection sequences.

As an alternative to the encoding device 48 being a bar code, the encoding device 48 also could include machine-readable raised or recessed surfaces. In addition, the tubular body 32 of the syringe 12 also may be provided with an indicating mechanism 52 for readily detecting the presence or absence of a liquid contrast media in the syringe 12. In this instance, the indicating mechanism 52 includes a plurality of integrally molded, textured dots on the syringe 12, which provide a visual indication of whether the syringe 12 contains liquid or air.

Accordingly, while the above injector and syringe apparatus have proven effective, the engagement reliability of the mounting assembly 14 discussed hereinabove was found to be insufficient. Accordingly, a need has arisen for a more reliable syringe/injector engagement interface.

SUMMARY

According to one aspect of the device of the present disclosure, provided is an injector system for injecting fluid that includes a syringe and an injector. The syringe includes: a body comprising a rearward end and a forward end; a plunger movably disposed within the body; at least one syringe drive paw positioned toward the rearward end of the body; and a syringe engagement flange positioned toward the rearward end of the body and extending around a circumference of the body. The injector includes: a housing having a front plate defining a syringe-receiving opening therein and a drive member at least partially disposed within the housing and operable to engage the plunger disposed within the syringe. The syringe latch has a plurality of latch members extending toward a center of the syringe-receiving opening and configured to move from a closed position to an open position when a force is applied thereto and from the open position to the closed position when the force is removed therefrom. The syringe engagement flange pushes against the plurality of latch members of the syringe latch to open the syringe latch as axial rearward motion is applied to the syringe relative to the syringe latch and the plurality of latch members return to the closed position to retain the syringe within the opening of the housing when the syringe is fully seated within the housing.

The injector may further include a syringe release gear that forms an enclosure for receiving the syringe when the syringe is fully seated within the housing. The syringe release gear may be mounted to a rear side of the front plate by at least one syringe release cam pin. The syringe release gear may also include an opening formed therein that is aligned with the syringe-receiving opening of the front plate. The opening in the syringe release gear may include a plurality of teeth formed around a circumference thereof. In addition, the syringe drive paw may be configured to engage the plurality of teeth of the opening of the syringe release gear.

The syringe may be disengaged from the injector after completion of an injection procedure by rotating the syringe. This causes rotation of the syringe release gear via the engagement between the syringe drive paw and the plurality of teeth of the syringe release gear. The plurality of latch members of the syringe latch are thereby forced into the open position which allows a user to remove the syringe from the housing of the injector. The syringe desirably includes two syringe drive paws that are positioned toward the rearward end of the body located 180° degrees apart.

The syringe latch may include two latch members, three latch members, or any other suitable number of latch members. Each of the plurality of latch members of the syringe latch may include a first portion and an arc-shaped second portion extending from the first portion. The arc-shaped second portion, when viewed in cross-section, may include a sloping face. The syringe latch may be manufactured from a polymeric material.

According to another aspect of the present disclosure, also provided is a method for engaging a syringe with an injector. The method includes: providing a syringe having a body with a rearward end and a forward end, a plunger movably disposed within the body, a syringe drive paw positioned toward the rearward end of the body, and a syringe engagement flange positioned toward the rearward end of the body and extending around a circumference of the body; providing an injector that includes a housing having a front plate defining a syringe-receiving opening therein, a drive member at least partially disposed within the housing and operable to engage the plunger disposed within the syringe; and a syringe latch mounted to a front side of the front plate and comprising a plurality of latch members extending toward a center of the syringe-receiving opening and configured to move from a closed position to an open position when a force is applied thereto and from the open position to the closed position when the force is removed therefrom; applying axial rearward motion to the syringe relative to the syringe latch such that the syringe engagement flange pushes against the plurality of latch members of the syringe latch to open the syringe latch; and returning the plurality of latch members of the syringe latch to the closed position to retain the syringe within the opening of the housing when the syringe is fully seated within the housing.

According to another aspect of the present disclosure, an injector system for injecting fluid may include a syringe having a body comprising a rearward end and a forward end, and a plunger movably disposed within the body, the plunger having at least one flexible leg extending toward the rearward end of the body. The injector system may further include an injector having
a housing having a front plate defining a syringe-receiving opening therein, a drive member at least partially disposed within the housing and operable to engage the plunger disposed within the syringe and releasably connect the at least one flexible leg to at least a portion of the drive member, a syringe release gear that forms an enclosure for receiving the syringe when the syringe is fully seated within the housing, the syringe release gear mounted to a rear side of the front plate, and a plunger release tube surrounding at least a portion of the drive member, the plunger release tube having a first end rotationally engaged with the syringe release gear. Rotation of the syringe release gear may rotate and axially move the plunger release tube relative to the drive member to engage the at least one flexible leg and release the at least one flexible leg from the drive member.

According to a further aspect of the present disclosure, the syringe release gear may be mounted to a rear side of the front plate by at least one syringe release cam pin. The syringe release cam pin may extend through the front plate. The syringe release gear may include an opening formed therein that is aligned with the syringe-receiving opening of the front plate. The opening in the syringe release gear may include a plurality of teeth formed around a circumference thereof. At least one syringe drive paw may be positioned toward the rearward end of the body and a syringe engagement flange may be positioned toward the rearward end of the body and extending around a circumference of the body. The injector may further include a syringe latch mounted to a front side of the front plate, the syringe latch comprising a plurality of latch members extending toward a center of the syringe-receiving opening and configured to move from a closed position to an open position when a force is applied thereto and from the open position to the closed position when the force is removed therefrom, The syringe engagement flange may push against the plurality of latch members of the syringe latch to open the syringe latch as axial rearward motion is applied to the syringe relative to the syringe latch and the plurality of latch members return to the closed position to retain the syringe within the opening of the housing when the syringe is fully seated within the housing. The syringe drive paw may be configured to engage a plurality of teeth formed on the syringe release gear. The syringe may be disengaged from the injector after completion of an injection procedure by rotating the syringe, which causes rotation of the syringe release gear via the engagement between the syringe drive paw and a plurality of teeth of the syringe release gear, thereby forcing the plurality of latch members into the open position and allowing a user to remove the syringe from the housing of the injector. Each of the plurality of latch members of the syringe latch may include a first portion and an arc-shaped second portion extending from first portion. The arc-shaped portion may include a slot formed therein. The syringe may include two syringe drive paws positioned toward the rearward end of the body and located 180° degrees apart.

According to another aspect of the present disclosure, a front-loading medical injector system may include a syringe having a body comprising a rearward end and a frontward end, and a plunger movably disposed within the body, the plunger having at least one flexible leg extending toward the rearward end of the body. The injector system may further include an injector having a housing having a front plate defining a syringe-receiving opening therein, a drive member at least partially disposed within the housing and operable to engage the plunger disposed within the syringe and releasably connect the at least one flexible leg to at least a portion of the drive member, and a syringe release assembly operable to release the syringe. Rotation of the syringe release assembly may release the at least one flexible leg from the drive member. The syringe release assembly may include a syringe release gear that forms an enclosure for receiving the syringe when the syringe is fully seated within the housing, the syringe release gear mounted to a rear side of the front plate, and a plunger release tube surrounding at least a portion of the drive member, the plunger release tube having a first end rotationally engaged with the syringe release gear. Rotation of the syringe release gear may rotate and axially move the plunger release tube relative to the drive member to engage the at least one flexible leg and release the at least one flexible leg from the drive member. The injector may further include a syringe latch mounted to a front side of the front plate for securing the syringe to the injector. The syringe latch may have a plurality of latch members extending toward a center of the syringe-receiving opening and configured to move from a closed position to an open position when a force is applied thereto and from the open position to the closed position when the force is removed therefrom. At least one syringe drive paw may be positioned toward the rearward end of the body, and a syringe engagement flange may positioned toward the rearward end of the body and extending around a circumference of the body. The syringe engagement flange may push against the plurality of latch members of the syringe latch to open the syringe latch as axial rearward motion is applied to the syringe relative to the syringe latch and the plurality of latch members return to the closed position to retain the syringe within the opening of the housing when the syringe is fully seated within the housing. Each of the plurality of latch members of the syringe latch may include a first portion and an arc-shaped second portion extending from first portion.

These and other features and characteristics of the device of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the device of the present disclosure. As used in the specification and the claims, the singular form of "a", "an", and "the" include plural referents unless the context clearly dictates otherwise.

DETAILED DESCRIPTION

Figure 1:
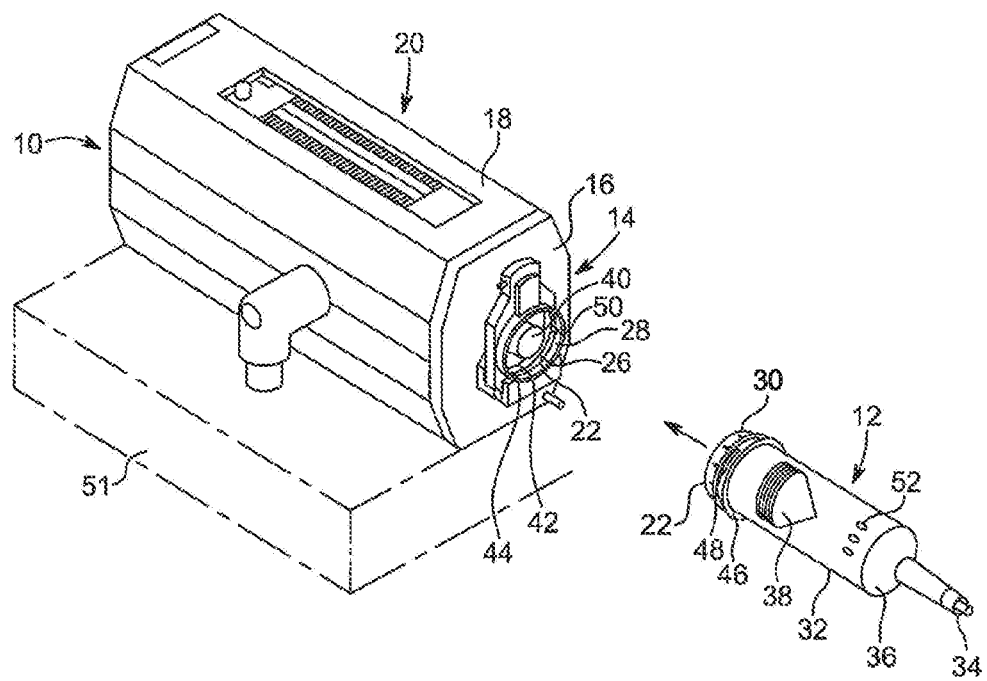
FIG. 1 is a perspective view of a conventional injector system showing an injector housing and a syringe in a disassembled relationship.

For purposes of the description hereinafter, the terms "upper", "lower", "right", "left", "vertical", "horizontal", "top", "bottom", "lateral", "longitudinal", and derivatives thereof, shall relate to the device of the present disclosure as it is oriented in the drawing figures. However, it is to be understood that the device of the present disclosure may assume various alternative variations, except where expressly specified to the contrary. It is also to be understood that the specific devices illustrated in the attached drawings, and described in the following specification, are simply exemplary embodiments of the device of the present disclosure. Hence, specific dimensions and other physical characteristics related to the embodiments disclosed herein are not to be considered as limiting.

Figure 2:
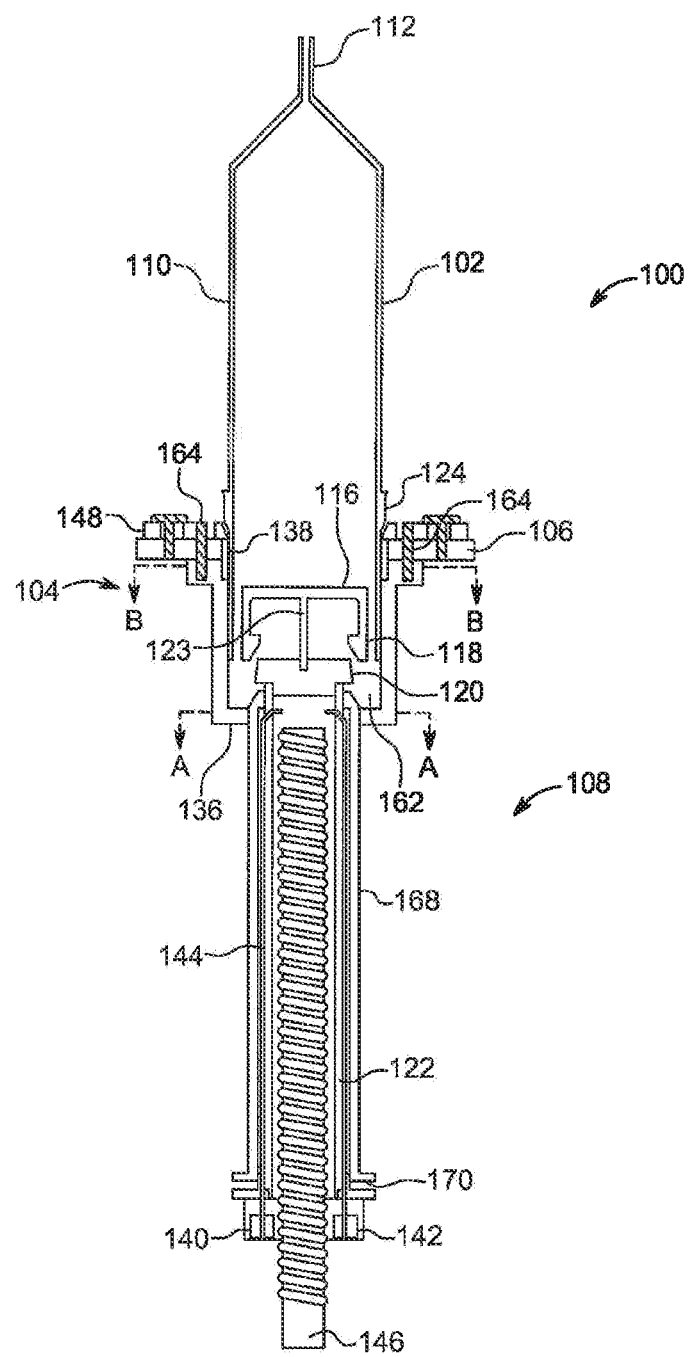
FIG. 2 is a cross-sectional view of an injector system in accordance with an embodiment of the disclosure showing the syringe and the injector housing in a partially disassembled relationship.

With reference to FIG. 2, an injector system 100 for injecting a liquid contrast media into a vascular system of an animal is provided. The injector system 100 has a front-loading construction. The system of FIG. 2 utilizes a syringe 102 capable of being front-loaded into a mounting assembly 104 associated with a front plate 106 of a housing (not shown) of an injector 108 by a first releasable mechanism 22. The syringe 102 is capable of functioning in an injection operation without the use of a pressure jacket (although the syringe may be used in an injector with a pressure jacket).

The syringe 102 includes an elongated main tubular body or barrel 110 and a coaxial discharge injection section 112 interconnected by an intermediate conical portion 114. A plunger 116 is slidably positioned within the tubular body 110 and includes at least one plunger connect flex leg 118 that is connectable to a piston/plunger interface 120 on a piston 122 of the injector 108. The plunger 116 also includes a plunger sense interrupter 123 extending from a central portion thereof in the direction of the at least one flex leg 118. The plunger sense interrupter 123 is configured to interrupt a light path produced by an IR transmitter 140 and IR receiver 142 through a fiber optic cable 144 extending along the length of the piston 122, thereby providing a signal to an injector controller (not shown) that the syringe 102 is fully seated within the injector 108. An alternative embodiment of the plunger sense interrupter 123 determines the presence/absence of the syringe 102 without the use of a fiber optic cable.

The syringe 102 further includes a syringe engagement flange 124 positioned toward the rearward end of the body 110 and extending around a circumference of the body 110. When viewed in cross-section, the syringe engagement flange 124 includes a sloping section 126, a shoulder section 128 extending from the sloping section 126 that is essentially perpendicular to an exterior surface of the body 110 of the syringe 102, and an engagement section 130 extending from the shoulder section 128. The engagement section 130 is configured to engage a plurality of teeth 132 of an opening 134 of a syringe release gear 136 of the injector 108 as discussed in greater detail hereinafter in relation to FIG. 6.

Since the syringe 102 is being used in this embodiment without a pressure jacket, for strength and visibility of the contents of the syringe 102, the syringe 102 may be formed of a clear PET polyester material. In the alternative, the wall of the syringe 102 may be formed of polypropylene reinforced by providing a series of annular ribs on the tubular body 110 of the syringe 102 in a longitudinally spaced relationship. In addition, the syringe 102 desirably includes an encoding device for providing information regarding the syringe 102 to the injector 108 an indicating mechanism for readily detecting the presence or absence of a liquid contrast media in the syringe 102 similar to the encoding device and indicating mechanism of syringe 12 discussed hereinabove.

With continued reference to FIG. 1, the injector includes a housing (not shown) having the front plate 106 defining a syringe-receiving opening 138 therein. The piston 122 is positioned within the housing and is configured to extending into and out of the syringe-receiving opening 138 under the power of a drive mechanism 146. The piston 122 includes the piston/plunger interface 120 at an end thereof that is operable to interact with the at least one flex leg 118 of the plunger 116 to engage the plunger 116 disposed within the syringe 102.

Figure 3:
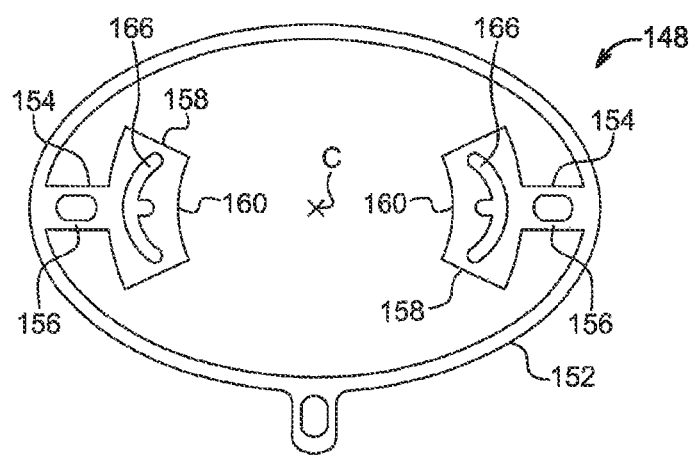
FIG. 3 is a top plan view of the syringe latch in accordance with an embodiment of the disclosure for connecting the syringe to the injector housing.

With reference to FIG. 3 and with continuing reference to FIG. 2, the injector 108 also includes a syringe latch 148 mounted to a front side of the front plate 106 by any suitable fastening device 150 for maintaining the syringe in the seated position within the injector 108. The syringe latch 148 comprises a substantially oval shaped body member 152 and a plurality of latch members 154 extending toward a center C of the body member 152. In the embodiment of the syringe latch 148 illustrated in FIG. 3, two latch members 154 are included. The syringe latch 148 is desirably manufactured from a resilient, polymeric material such that the latch members 154 are configured to move from a closed position to an open position when a force is applied thereto and from the open position to the closed position when the force is removed therefrom.

Each of the plurality of latch members 154 of the syringe latch 148 includes a first portion 156 extending from the body member 152 and an arc-shaped second portion 158 extending from the first portion 156 and configured to engage the syringe engagement flange 124 of the syringe 102. The arc-shaped second portion 158, when viewed in cross-section, may include a sloping face 160 (see FIGS. 4A-4E) that engages with the sloping section 126 of the syringe engagement flange 124 to force the syringe latch 148 into the open position.

With continued reference to FIG. 2, the injector 108 also includes the syringe release gear 136 that forms an enclosure 162 for receiving the syringe 102 when the syringe 102 is fully seated within the injector housing. The syringe release gear 136 is mounted to a rear side of the front plate 106 by at least one syringe release cam pin 164. The syringe release cam pin 164 is configured to be connected to the syringe release gear 136 and extend through the front plate 106 of the injector 108 into a slot 166 in the arc-shaped second portion 158 of the latch members 154 of the syringe latch 148.

Figure 7:
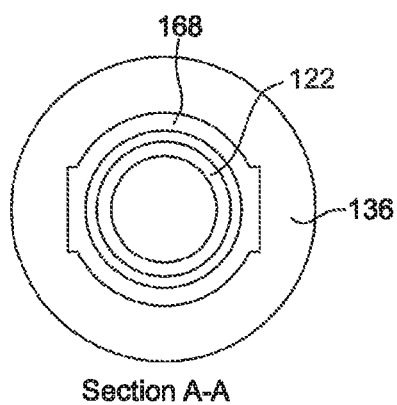
FIG. 7 is a cross-sectional view of the injector system of FIG. 2 taken along line A-A.

With reference to FIG. 7 and with continued reference to FIG. 2, the piston 122 is surrounded by a plunger release tube 168. The plunger release tube 168 has a first end that is rotationally engaged with the syringe release gear 136 such that rotation of the syringe release gear 136 causes rotation of the plunger release tube 168.

The process for engaging a syringe 102 with the injector 108 to form an injector system 100 is illustrated in FIGS. 4A-4E. This process allows for syringe engagement with an injector 108 that provides a syringe engagement adapted to releasably engage the syringe 102 with the injector 108 regardless of the rotational orientation of the syringe 102 with respect to the injector 108. The syringe engagement uses the flex legs 118 attached to the back side of the plunger 116 of the syringe 102 and a corresponding feature on the piston 122 of an injector 108 that provides axial engagement that does not require any specific rotational orientation of the syringe 102 to releasably engage with the injector 108. Additionally, a feature (i.e., the syringe engagement flange 124) is provided on the outside surface of the rear portion of the tubular body 110 to transfer rotational movement of the syringe into a release mechanism (i.e., the syringe release gear 136) implemented in the injector 108 releasing both the syringe 102 and the plunger 116 regardless of the axial position of the engaged syringe plunger 116.

Figure 4A:
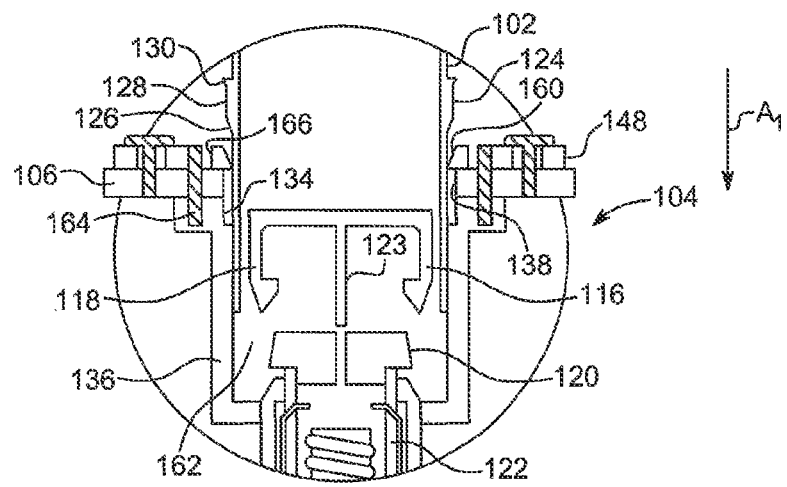
FIGS. 4A-4E are cross-sectional views of a portion of the injector system of FIG. 2 illustrating the steps required for loading a syringe into the injector housing.
Figure 4B:
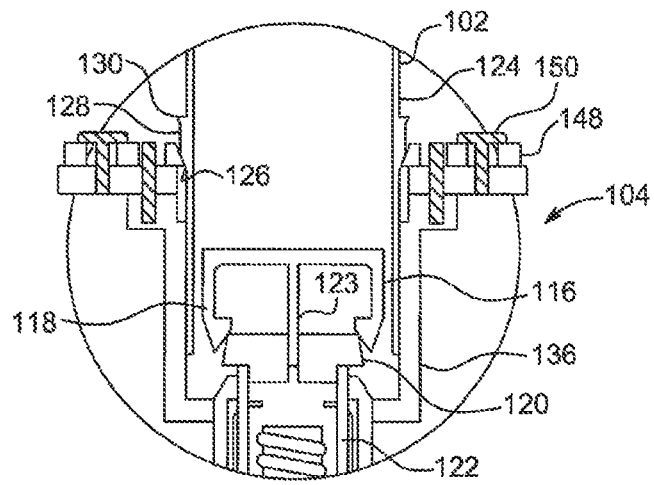
Figure 4C:
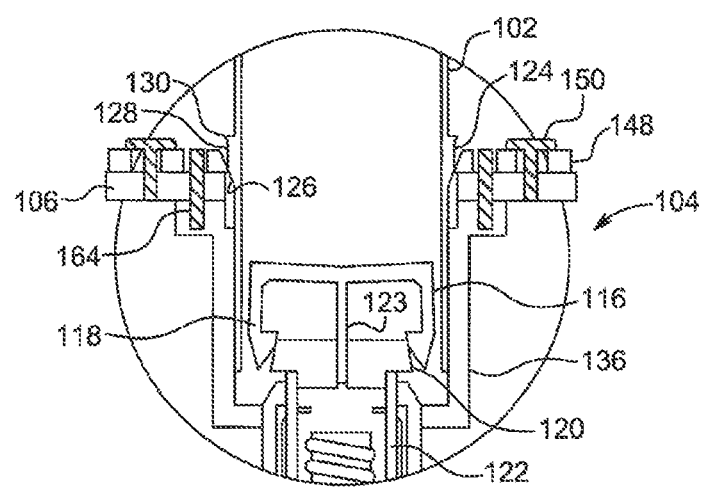
Figure 4D:
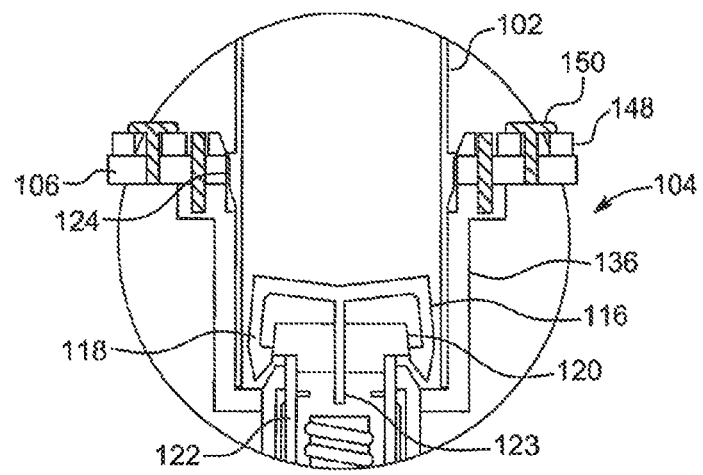
Figure 4E:
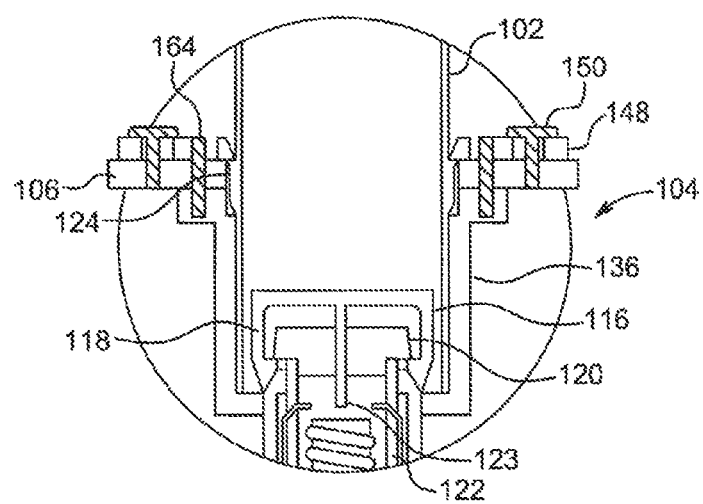

The first step in the process for engaging the syringe 102 with the injector 108 is shown in FIG. 4A in which the syringe 102 is positioned axially with the syringe-receiving opening 134 of the front plate 106 of the injector 108 and is moved axially along the piston 122 into the enclosure 162 formed by the syringe release gear 136 in the direction of arrow $A_1$. With reference to FIG. 4B, as the syringe 102 is inserted, the sloping section 126 of the syringe engagement flange 124 engages the sloping face 160 of the arc-shaped second section 158 of the latch members 154 of the syringe latch 148 and pushes the syringe latch 148. In addition, with reference to FIGS. 4C and 4D, as the syringe 102 is inserted, the sloped surface of the piston/plunger interface 120 flexes the at least one flex leg 118 of the plunger 116 open. With reference to FIG. 4E, continual movement of the syringe 102 in the direction of arrow $A_1$ causes the syringe 102 to be fully seated within the enclosure 162 formed by the syringe release gear 136. When the body of the syringe 102 is fully seated within the enclosure 162 formed by the syringe release gear 136, the following items occur: first, the engagement section 130 of the syringe engagement flange 124 engages the teeth 132 of the syringe release gear 136. In addition, the syringe engagement flange 124 moves beyond the arc-shaped second portion 158 of the latch members 154 of the syringe latch 148, thereby closing the syringe latch 148 to retain the syringe 102. Desireably, when the syringe latch 148 returns to the closed position, it provides an audible "click" to indicate to the operator that the syringe 102 has been installed on the injector 108. Furthermore, the flex legs 118 on the plunger 116 flex closed engaging the piston/plunger interface 120. Finally, the plunger sense interrupter 123 of the plunger 116 interrupts the light path produced by an IR transmitter 140 and IR receiver 142 through a fiber optic cable 144 extending along the length of the piston 122, thereby providing a signal to an injector controller (not shown) that the syringe 102 is fully seated within the injector 108.

Removal of the syringe 102 from the injector 108 upon the completion of an injection procedure requires that the syringe 102 be rotated, as described below. This operation is illustrated in and described by reference to FIGS. 8A-8D.

Figure 6:
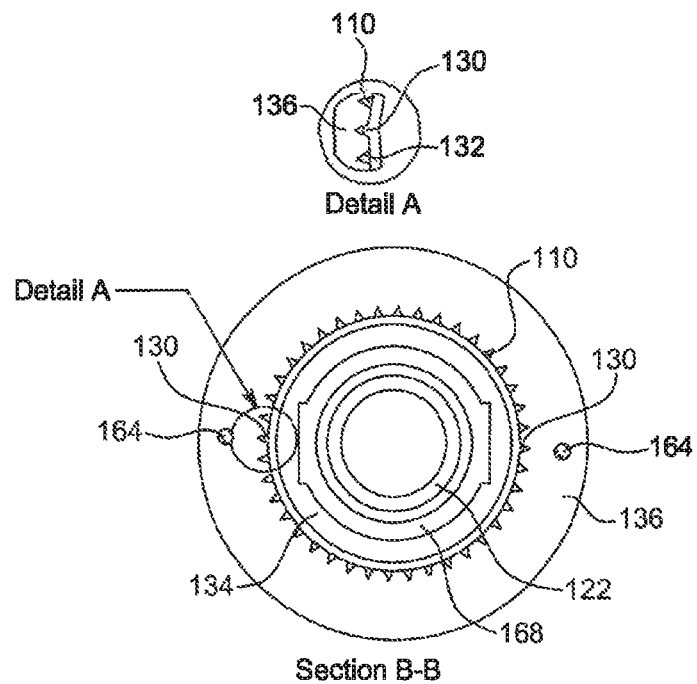
FIG. 6 is a cross-sectional view of the injector system of FIG. 2 taken along line B-B.
Figure 8A:
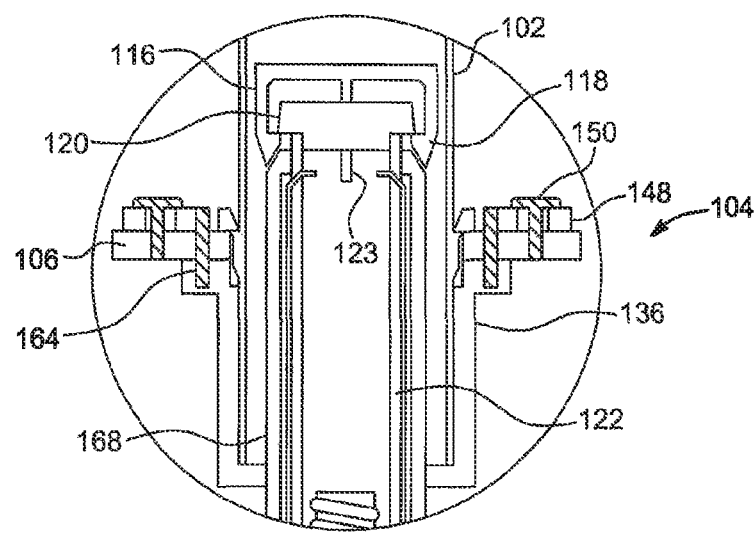
FIGS. 8A-8D are cross-sectional views of a portion of the injector system of FIG. 5 illustrating the steps required for unloading a syringe from the injector housing.
Figure 8B:
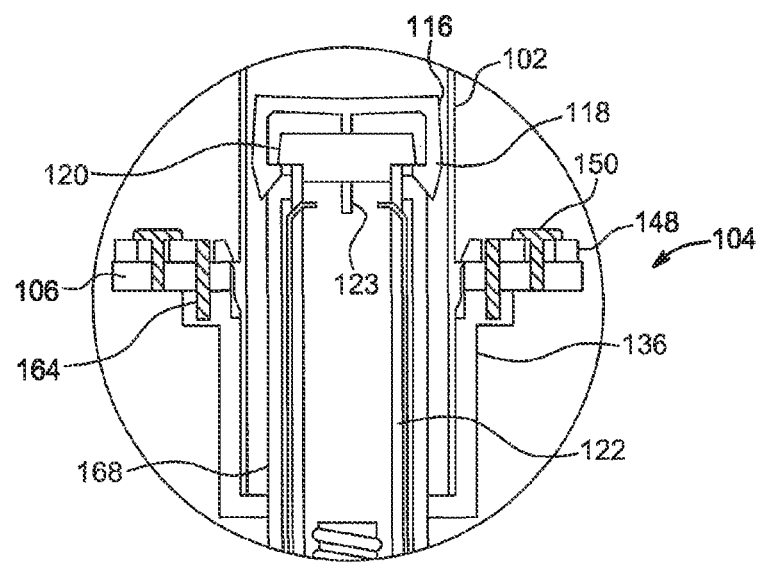
Figure 8C:
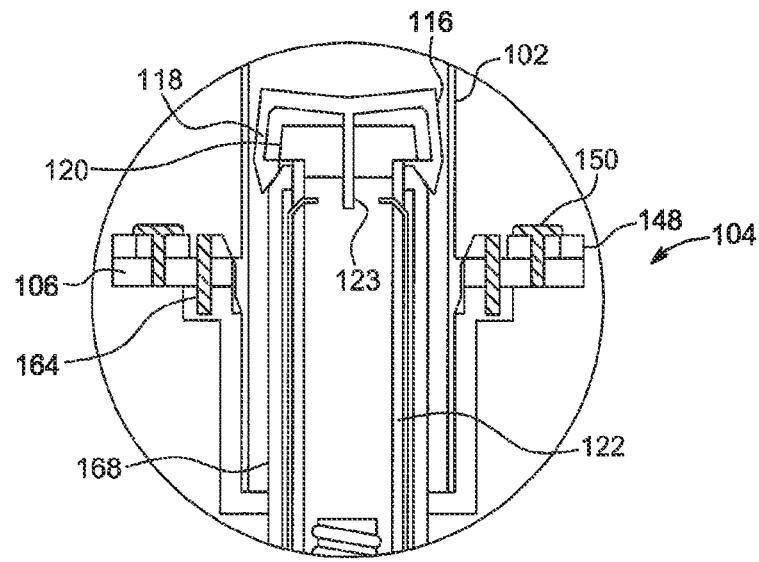

With reference to FIG. 8A and FIG. 8B, the rotation of the syringe 102 causes rotation of the syringe release gear 136 via the engagement between the engagement section 130 of the syringe engagement flange 124 and the plurality of teeth 132 of the syringe release gear 136 as shown in FIG. 6. This rotation, in turn, causes rotation of the syringe release cam pins 164 along the slots 166 provided in the latch members 154 of the syringe latch 148 as shown in FIG. 8C. The latch members 154 of the syringe latch 148 are thereby forced into the open position.

Figure 5:
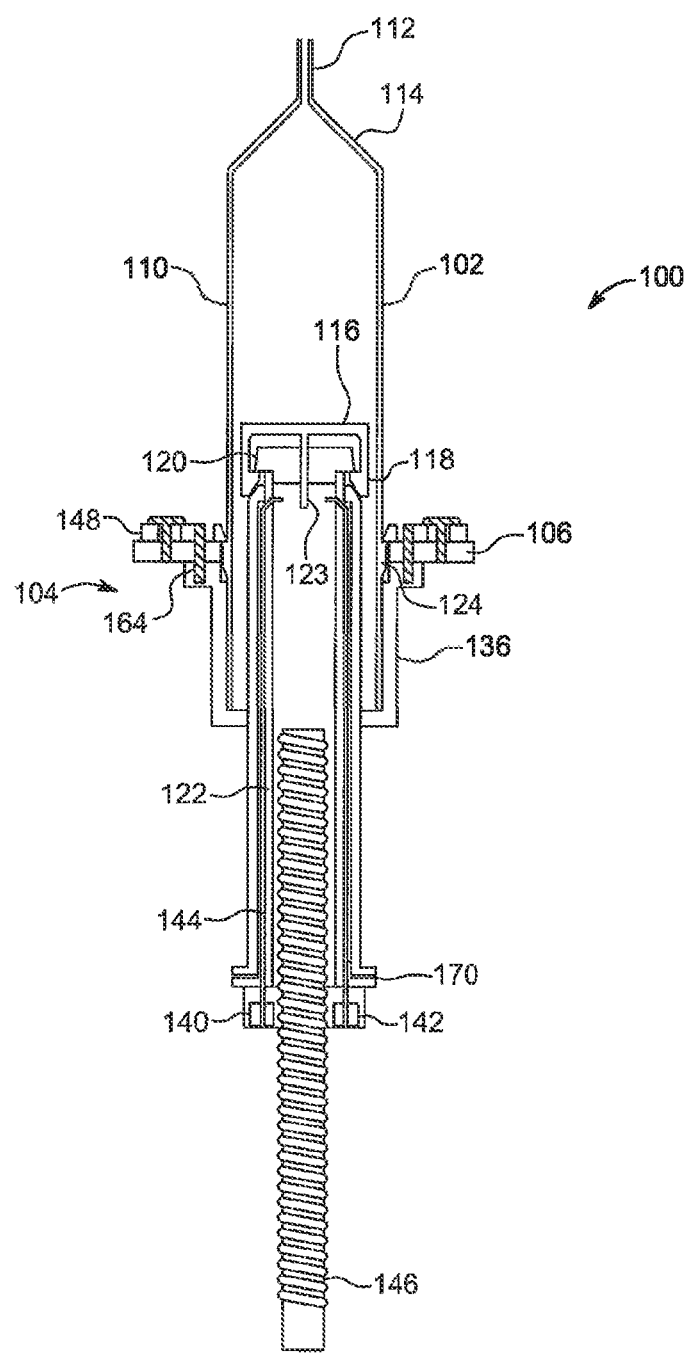
FIG. 5 is a cross-sectional view of the injector system of FIG. 2 showing the syringe and the injector housing in the assembled state.

As also shown in FIG. 8C, the rotation of the syringe release gear 136 also rotates the plunger release tube 168 about the piston 122 since the plunger release tube 168 is coupled to the syringe release gear 136 as described hereinabove. The rotation of the plunger release tube 168 about the piston 122 causes a cam action at a release cam surface 170 (see FIGS. 1 and 5) causing an axial extension of the plunger release tube 168 towards the syringe-receiving opening 134 of the front plate 106. The axial extension of the plunger release tube 168 forces the at least one flex leg 118 of the plunger 116 to flex open to release the piston/plunger interface 122.

Figure 8D:
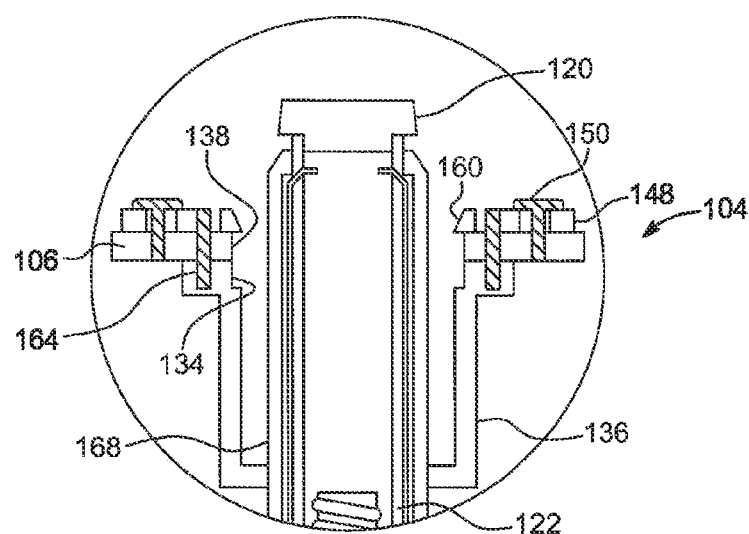
Figure 9:
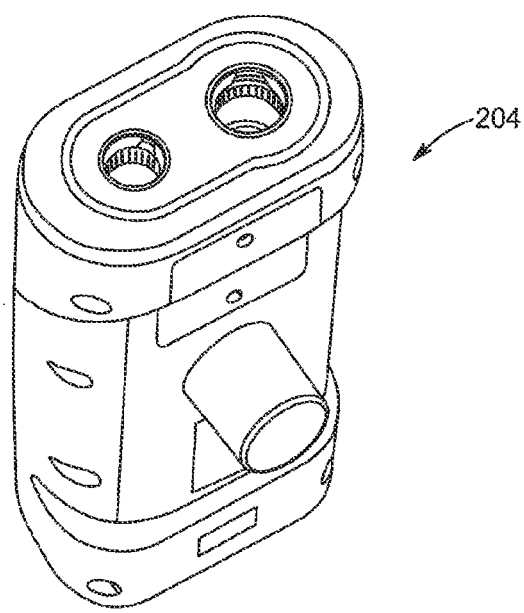
FIG. 9 is a perspective view of an injector in accordance with an alternative embodiment of the disclosure.

At this point, a user can remove the syringe 102 from the housing of the injector 108. Once the syringe 102 is removed, the syringe release gear 136 returns to original position allowing the syringe latch 148 to return to the closed position and the plunger release tube 168 to drop down as shown in FIG. 8D.

Figure 10:
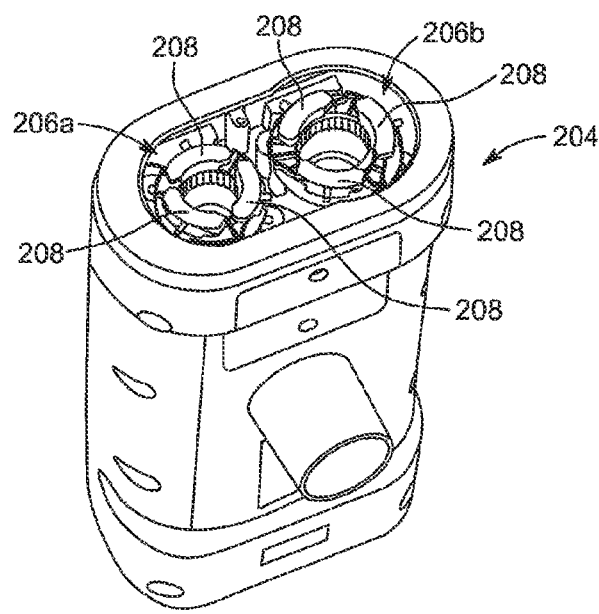
FIG. 10 is a perspective view of the injector of FIG. 9 having the faceplate removed such that an alternative embodiment of the syringe latch is visible.
Figure 11:
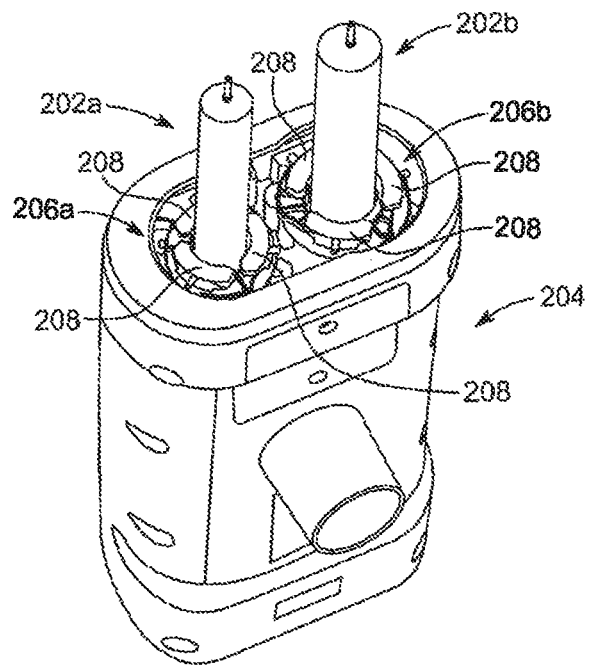
FIG. 11 is a perspective view of the injector of FIG. 10 with syringes attached thereto.
Figure 12:
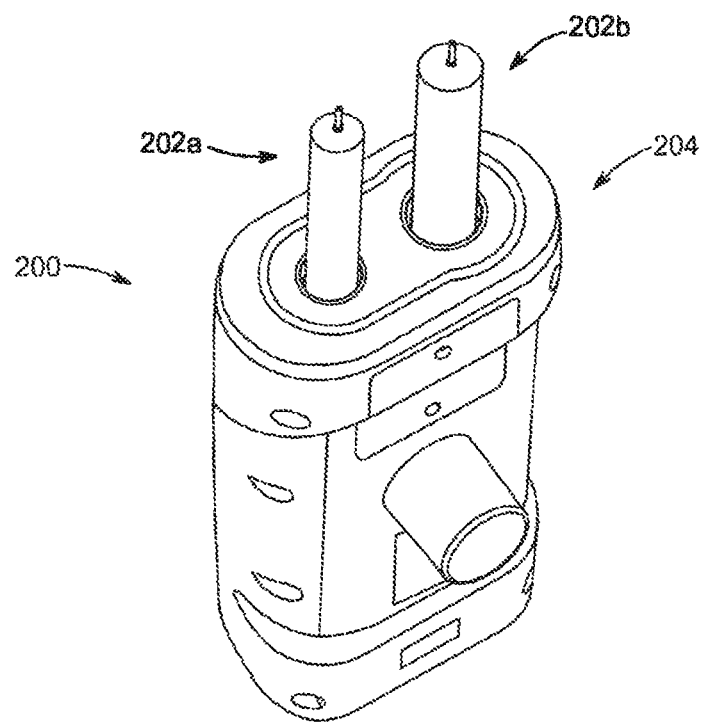
FIG. 12 is a perspective view of the injector of FIG. 9 with syringes attached thereto.

While the syringe latch 148 discussed hereinabove includes two latch members, this is not to be construed as limiting the disclosure as any suitable number of latch members may be utilized. For instance, with reference to FIGS. 9-14, the injector may be embodied as a dual syringe injector system 200 that includes a pair of syringes 202a, 202b and an injector 204. As shown in FIGS. 10 and 11, the injector 204 utilizes a syringe latch 206a, 206b for each of the syringes 202a, 202b that includes three latch members 208 for engaging the syringe 202a, 202b within the injector 204. In addition, rather than having the latch members 208 connected to a body member as with the syringe latch 148 discussed hereinabove, each of the latch members 208 is independent and utilizes a spring return 210 (see FIG. 14).

Figure 13:
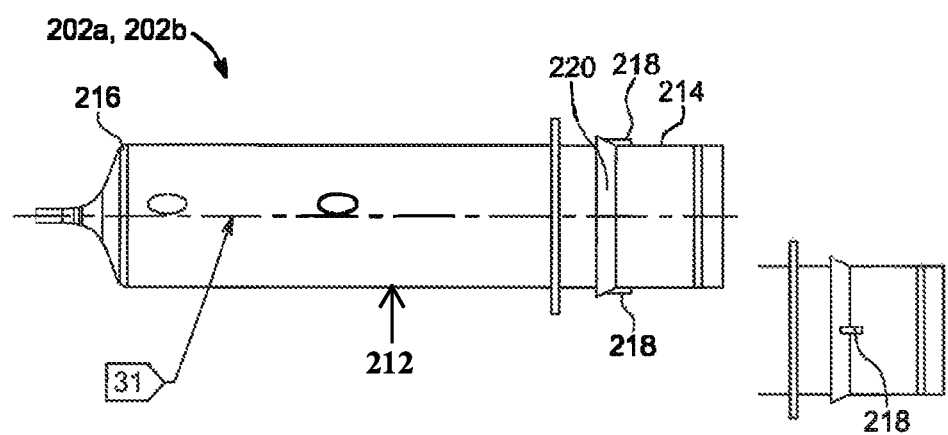
FIG. 13 is a side view of a syringe configured to be used with the injector of FIG. 9.
Figure 14:
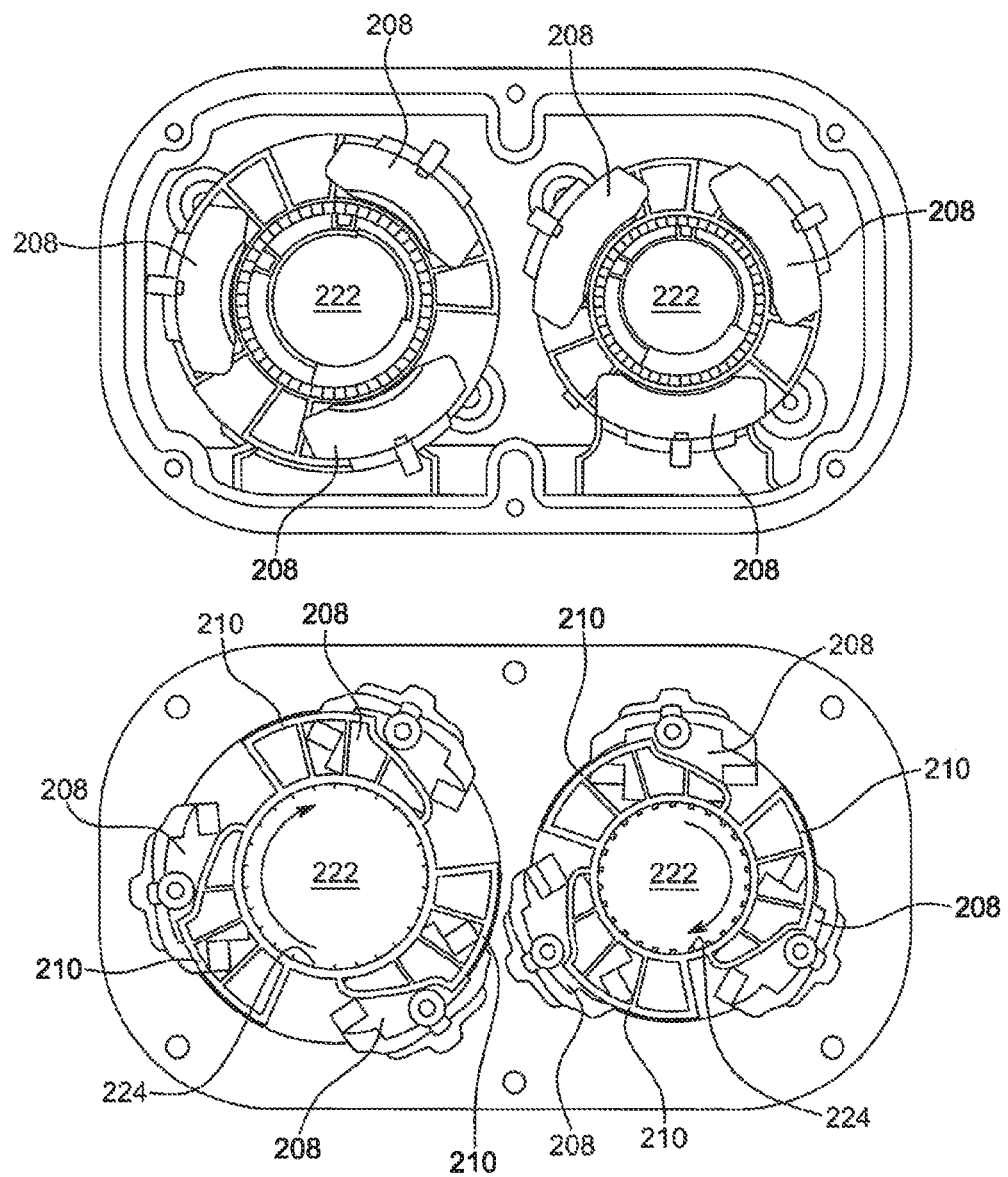
FIG. 14 is front views of the syringe latch of the injector of FIG. 9.

More specifically, with reference to FIGS. 13 and 14, a syringe 202a, 202b for use with injector 204 includes a body 212 comprising a rearward end 214 and a forward end 216; a plunger (not shown) movably disposed within the body 212; and at least one syringe drive paw 218 positioned toward the rearward end 214 of the body 212. Desirably, the syringe 202a, 202b includes a pair of syringe drive paws 218 at the rearward end 214 of the body 212 located 180° apart. The syringe 202a, 202b also includes a syringe engagement flange 220 positioned toward the rearward end 214 of the body 212 and extending around a circumference of the body 212.

The injector 204 includes a pair of syringe latches 206a, 206b mounted to a front side of the front plate thereof. Each of the syringe latches 206a, 206b comprises a plurality of latch members 208 extending toward a center of the syringe-receiving opening 222 and configured to move from a closed position to an open position when a force is applied thereto and from the open position to the closed position when the force is removed therefrom. The syringe engagement flange 220 pushes against the plurality of latch members 208 of the syringe latch 206a, 206b to open the syringe latch 206a, 206b as axial rearward motion is applied to the syringe 202a, 202b relative to the syringe latch 206a, 206b and the plurality of latch members 208 return to the closed position to retain the syringe 202a, 202b within the opening 222 of the injector 204 when the syringe 202a, 202b is fully seated within the injector 204.

The syringe 202a, 202b may be disengaged from the injector 204 after completion of an injection procedure by rotating the syringe 202a, 202b. This causes rotation of a syringe release gear 224 via the engagement between the syringe drive paws 218 and a plurality of teeth of the syringe release gear 224. The rotation of the syringe release gear 224 activates the spring returns 210, which force the latch members 208 of the syringe latch 206a, 206b into the open position, thereby allowing a user to remove the syringe 202a, 202b from the injector 204.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

We claim:

1. A syringe for interfacing with a fluid injector comprising at least one syringe latch for maintaining the syringe in operable engagement with the fluid injector, and a syringe release mechanism for releasing the syringe from operable engagement with the fluid injector, the syringe comprising:
   an elongated tubular body comprising a rearward end and a forward end;
   a plunger movably disposed within the tubular body, the plunger having at least one flexible leg extending toward the rearward end of the tubular body and configured to be releasably connectable to a piston of the fluid injector;
   a syringe engagement flange positioned toward the rearward end of the tubular body and extending around a circumference of the tubular body, the syringe engagement flange comprising:
      a sloping section configured to engage the at least one syringe latch; and
      an engagement section adjoined with the sloping section and configured to engage the syringe release mechanism,
   wherein the syringe engagement flange transfers movement imparted to the syringe by a user into the syringe release mechanism to force the at least one syringe latch into an open position to release the syringe and cause a plunger release tube to release the plunger from the piston of the fluid injector regardless of an axial position of the plunger with the piston of the fluid injector, such that both the syringe and the plunger are released by the movement imparted to the syringe by the user.

2. The syringe of claim 1, wherein the syringe engagement flange further comprises a shoulder section extending proximally from the sloping section that is essentially perpendicular to an exterior surface of the tubular body.

3. The syringe of claim 1, wherein the movement imparted to the syringe by the user is rotational movement.

4. The syringe of claim 3, wherein the syringe release mechanism comprises a syringe release gear and a plurality of teeth arranged around an opening of the syringe release gear, wherein the engagement section of the syringe engagement flange is adapted to engage the plurality of teeth of the syringe release gear such that the rotational movement of the syringe causes rotation of the syringe release gear via engagement between the engagement section of the syringe engagement flange and the plurality of teeth of the syringe release gear.

5. The syringe of claim 1, wherein the at least one flexible leg is operable to interact with a piston/plunger interface of the piston of the fluid injector.

6. The syringe of claim 1, wherein the syringe engagement flange extends completely around a circumference of the tubular body.

7. The syringe of claim 1, wherein the syringe includes a coaxial discharge injection section interconnected by an intermediate conical portion to the tubular body.

8. An injector system for injecting a fluid, comprising:
a syringe, comprising:
an elongated tubular body comprising a rearward end and a forward end;
a plunger movably disposed within the tubular body, the plunger having at least one flexible leg extending toward the rearward end of the tubular body;
a syringe engagement flange positioned toward the rearward end of the tubular body and extending around a circumference of the tubular body, the syringe engagement flange comprising:
a sloping section; and
an engagement section adjoined with the sloping section;
a fluid injector, comprising:
a piston operable to engage the plunger disposed within the syringe, the at least one flexible leg releasably connectable to the piston of the fluid injector such that the piston is operable to move the plunger within the tubular body;
a syringe release mechanism that forms an enclosure for receiving the syringe into the fluid injector, the engagement section configured to engage the syringe release mechanism; and
at least one syringe latch for maintaining the syringe in operable engagement with the fluid injector, the sloping section configured to engage the at least one syringe latch to open the at least one syringe latch when the syringe is inserted into the enclosure; and
wherein the syringe engagement flange transfers movement imparted to the syringe by a user into the syringe release mechanism to force the at least one syringe latch into an open position to release the syringe and cause a plunger release tube to release the plunger from the piston of the fluid injector regardless of an axial position of the plunger with the piston of the fluid injector, such that both the syringe and the plunger are released by the movement imparted to the syringe by the user.

9. The syringe of claim 8, wherein the syringe engagement flange further comprises a shoulder section extending proximally from the sloping section that is essentially perpendicular to an exterior surface of the tubular body.

10. The injector system of claim 8, wherein the movement imparted to the syringe by the user is rotational movement.

11. The injector system of claim 10, wherein the syringe release mechanism comprises a syringe release gear and a plurality of teeth arranged around an opening of the syringe release gear, wherein the syringe engagement section is adapted to engage the plurality of teeth of the syringe release gear such that the rotational movement of the syringe causes rotation of the syringe release gear via engagement between the engagement section of the syringe engagement flange and the plurality of teeth of the syringe release gear.

12. The injector system of claim 11, wherein the plunger release tube surrounds at least a portion of the piston, the plunger release tube having a first end rotationally engaged with the syringe release gear and a second end opposite the first end,
wherein rotation of the syringe release gear rotates the plunger release tube and rotation of the plunger release tube causes a cam action at a release cam surface provided at the second end of the plunger release tube causing an axial extension of the plunger release tube relative to the piston such that the plunger release tube engages the at least one flexible leg and releases the at least one flexible leg from the piston.

13. The injector system of claim 8, wherein the at least one flexible leg is operable to interact with a piston/plunger interface of the piston of the injector.

14. The injector system of claim 8, wherein the syringe engagement flange extends completely around a circumference of the tubular body.

15. The injector system of claim 8, wherein the syringe includes a coaxial discharge injection section interconnected by an intermediate conical portion to the tubular body.

16. A syringe mounting assembly, comprising:
a front plate for a fluid injector, the front plate defining a syringe-receiving opening; and
a syringe release mechanism associated with the front plate, comprising:
at least one syringe latch mounted to a front side of the front plate for maintaining a syringe in operable engagement with the fluid injector, the at least one syringe latch configured to move from a closed position engaging the syringe to an open position when a force is applied and move from the open position to the closed position when the force is removed; and
a syringe release gear mounted to a rear side of the front plate and forming an enclosure around the syringe when the syringe is inserted into the syringe-receiving opening in the front plate; and
a syringe, comprising:
an elongated tubular body comprising a rearward end and a forward end;
a plunger movably disposed within the tubular body;
a syringe engagement flange positioned toward the rearward end of the tubular body and extending around a circumference of the tubular body, the syringe engagement flange comprising:
a sloping section configured to engage the at least one syringe latch; and
an engagement section adjoined with the sloping section and configured to engage the syringe release gear, wherein the sloping section is adapted to engage the at least one syringe latch to move the at least one syringe latch to the open position as the syringe is inserted into the syringe-receiving opening, and the engagement section is adapted to engage with teeth of the syringe release gear as the syringe is fully seated within the enclosure formed by the syringe release gear, wherein as the engagement section moves beyond the at least one syringe latch as the syringe is fully seated within the enclosure formed by the syringe release gear, the at least one syringe latch moves to the closed position to retain the syringe, and wherein the syringe engagement flange transfers movement imparted to the syringe by a user into the syringe release mechanism to force the at least one syringe latch into the open position to release the syringe and cause a plunger release tube to release the plunger from a piston of the fluid injector regardless of an axial position of the plunger with the piston of the fluid injector, such that both the syringe and the plunger are released by the movement imparted to the syringe by the user.

17. The syringe mounting assembly of claim 16, further comprising at least one syringe release cam pin extending into a slot in the at least one syringe latch to apply rotational motion to the at least one syringe latch, and wherein rotation of the syringe once the syringe is fully seated within the enclosure formed by the syringe release gear causes rotation of the syringe release gear via engagement between the engagement section of the syringe engagement flange and the teeth of the syringe release gear which, in turn, causes rotation of the syringe release cam pin in the slot in the at least one syringe latch imparting the rotational motion to the at least one syringe latch and moving the at least one syringe latch to the open position.

18. The syringe mounting assembly of claim 16, wherein the at least one syringe latch comprises a substantially oval shaped body member and a plurality of latch members extending toward a center of the body member.

19. The syringe mounting assembly of claim 18, wherein each of the latch member comprises a first portion extending from the body member and an arc-shaped second portion extending from the first portion, the arc-shaped second portion comprising a sloping face configured to engage with the sloping section of the syringe engagement flange.

20. The syringe mounting assembly of claim 16, wherein the syringe engagement flange extends completely around a circumference of the tubular body.

* * * * *

UNITED STATES PATENT AND TRADEMARK OFFICE
CERTIFICATE OF CORRECTION

PATENT NO. : 11,383,029 B2
APPLICATION NO. : 17/404272
DATED : July 12, 2022
INVENTOR(S) : Lang et al.

It is certified that error appears in the above-identified patent and that said Letters Patent is hereby corrected as shown below:

In the Specification
In Column 5, Line 35, delete "may" and insert -- may be --, therefor.
In Column 9, Lines 37-38, delete "piston/plunger interface 122." and insert -- piston/plunger interface 120. --, therefor.

In the Claims
In Column 12, Line 1, in Claim 9, delete "syringe" and insert -- injector system --, therefor.

Signed and Sealed this
Twenty-third Day of August, 2022

*Katherine Kelly Vidal*

Katherine Kelly Vidal
*Director of the United States Patent and Trademark Office*